United States Patent
Ogata et al.

(10) Patent No.: US 10,473,598 B2
(45) Date of Patent: Nov. 12, 2019

(54) X-RAY THIN FILM INSPECTION DEVICE

(71) Applicant: RIGAKU CORPORATION, Akishima-shi, Tokyo (JP)

(72) Inventors: Kiyoshi Ogata, Tokyo (JP); Sei Yoshihara, Saitama (JP); Takao Kinefuchi, Tokyo (JP); Shiro Umegaki, Tokyo (JP); Shigematsu Asano, Tokyo (JP); Katsutaka Horada, Tokyo (JP); Muneo Yoshida, Kanagawa (JP); Hiroshi Motono, Tokyo (JP); Hideaki Takahashi, Tokyo (JP); Akifusa Higuchi, Tokyo (JP); Kazuhiko Omote, Tokyo (JP); Yoshiyasu Ito, Tokyo (JP); Naoki Kawahara, Osaka (JP); Asao Nakano, Kanagawa (JP)

(73) Assignee: RIGAKU CORPORATION, Akishima-shi, Tokyo (JP)

( * ) Notice: Subject to any disclaimer, the term of this patent is extended or adjusted under 35 U.S.C. 154(b) by 323 days.

(21) Appl. No.: 15/518,892

(22) PCT Filed: Oct. 14, 2014

(86) PCT No.: PCT/JP2014/077335
§ 371 (c)(1),
(2) Date: Apr. 13, 2017

(87) PCT Pub. No.: WO2016/059672
PCT Pub. Date: Apr. 21, 2016

(65) Prior Publication Data
US 2017/0234814 A1   Aug. 17, 2017

(51) Int. Cl.
*H05G 1/02* (2006.01)
*A61B 6/08* (2006.01)
*G01N 23/20* (2018.01)
*G01N 23/223* (2006.01)
(Continued)

(52) U.S. Cl.
CPC ......... *G01N 23/223* (2013.01); *G01N 23/203* (2013.01); *G01N 23/2204* (2013.01);
(Continued)

(58) Field of Classification Search
CPC ..... G01N 2223/076; G01N 2223/1016; G01N 23/20016; G01N 23/20025; G01N 23/2204; G01N 23/223
See application file for complete search history.

(56) References Cited

U.S. PATENT DOCUMENTS

| | | | | |
|---|---|---|---|---|
| 7,258,485 B2 * | 8/2007 | Nakano | ............ | G01N 23/20016 378/196 |
| 2006/0088139 A1 * | 4/2006 | Nakano | ............ | G01N 23/20016 378/79 |
| 2017/0299528 A1 * | 10/2017 | Ogata | .................. | G01N 23/223 |

FOREIGN PATENT DOCUMENTS

| | | |
|---|---|---|
| JP | 9-15392 A | 1/1997 |
| JP | 9-218170 A | 8/1997 |

(Continued)

OTHER PUBLICATIONS

International Search Report dated Feb. 17, 2015, issued in counterpart International Application No. PCT/JP2014/077335 (2 pages).
(Continued)

*Primary Examiner* — Don K Wong
(74) *Attorney, Agent, or Firm* — Westerman, Hattori, Daniels & Adrian, LLP

(57) ABSTRACT

An X-ray thin film inspection device of the present invention includes an X-ray irradiation unit 40 installed on a first rotation arm 32, an X-ray detector 50 installed on a second rotation arm 33, and a fluorescence X-ray detector 60 for detecting fluorescence X-rays generated from an inspection target upon irradiation of X-rays. The X-ray irradiation unit 40 includes an X-ray optical element 43 comprising a confocal mirror for receiving X-rays radiated from an X-ray
(Continued)

tube 42, reflects plural focused X-ray beams monochromatized at a specific wavelength and focuses the plural focused X-ray beams to a preset focal point, and a slit mechanism 46 for passing therethrough any number of focused X-ray beams out of the plural focused X-ray beams reflected from the X-ray optical element 43.

19 Claims, 29 Drawing Sheets

(51) Int. Cl.
*G01N 23/2204* (2018.01)
*G01N 23/203* (2006.01)
*G01N 23/2206* (2018.01)
(52) U.S. Cl.
CPC ... *G01N 23/2206* (2013.01); *G01N 2223/076* (2013.01); *G01N 2223/315* (2013.01); *G01N 2223/61* (2013.01); *G01N 2223/6116* (2013.01)

(56) References Cited

FOREIGN PATENT DOCUMENTS

| JP | 10-2998 A | 1/1998 |
| JP | 2006-153767 A | 6/2006 |
| JP | 4759750 B2 | 8/2011 |

OTHER PUBLICATIONS

International Search Report dated Feb. 17, 2015, issued in International Application No. PCT/JP2014/077336, which is counterpart to co-pending U.S. Appl. No. 15/518,095 (in English; 1 page).
Office Action dated Mar. 29, 2019, issued in co-pending U.S. Appl. No. 15/518,095 (w/ returned PTO/SB/08a form; in English; 13 pages).

\* cited by examiner

201

X-RAY THIN FILM INSPECTION DEVICE

TECHNICAL FIELD

The present invention relates to an X-ray thin film inspection device suitable for use in a semiconductor manufacturing field, etc., such as a technical field for manufacturing an element having a multilayer structure in which many thin films are laminated on a substrate.

BACKGROUND ART

The characteristics of a semiconductor, etc., such as an element having a multilayer structure in which many thin films are laminated on a substrate, vary according to the state of a film to be formed, such as the film thickness, density, crystalline, etc. of the film. Microfabrication and integration of these elements have recently progressed, and this tendency has become remarkable. Therefore, a thin film inspection device that is capable of accurately measuring the states of formed films have been required.

As this type of inspection device have been known direct measurement based on a cross-section transmission electron microscope (TEM), a film thickness inspection device using optical interference or ellipsometry, a photoacoustic device, etc. The present situation of the cross-sectional transmission electron microscope (TEM) is that it is impossible to install the cross-sectional transmission electron microscope in an in-line manufacturing process and inspect a thin film as an inspection target in real time, and also a product which is extracted for an inspection from the manufacturing line is discarded after the inspection. Furthermore, the film thickness inspection device using optical interference or ellipsometry and the photoacoustic device are suitable for the in-line process, but have insufficient precision for measurements of thin films of several nm.

Wafers for inspection which are discarded after used (blanket wafers) have imposed a large burden in cost on semiconductor device makers. Particularly, the diameter of semiconductor wafers has recently increased, so that the cost of one blanket wafer has also increased.

DISCLOSURE OF THE INVENTION

Problem to be Solved by the Invention

Therefore, the applicant of the present application has proposed an X-ray thin film inspection device that can be installed in a process of manufacturing film-formed products, directly inspect the products themselves and can inspect even a thin film of several nm with sufficient precision without discarding a wafer after use (see Patent Document 1: JP-A-2006-153767).

Furthermore, the applicant of the present application has repetitively improved the previously proposed X-ray thin film inspection device, and has reached completion of the present invention.

Means of Solving the Problem

That is, according to the present invention, an X-ray thin film inspection device comprises:
a sample stage having an upper surface on which an inspection target is disposed;
an image observing unit that is adapted to observe an image of the inspection target disposed on the upper surface of the sample stage;
a positioning mechanism that is controlled based on an image observation result of the inspection target by the image observing unit to move the sample stage in two directions perpendicular to each other on a horizontal plane, the two directions being a height direction and an in-plane rotating direction;
a goniometer having a first rotation member and a second rotation member that rotate along a virtual flat plane perpendicular to the upper surface of the sample stage;
an X-ray irradiation unit installed on the first rotation member;
an X-ray detector installed on the second rotation member; and
a fluorescence X-ray detector that detects fluorescence X-rays generated from the inspection target upon irradiation of X-rays.

Here, the X-ray irradiation unit comprises:
an X-ray tube that radiates X-rays;
an X-ray optical element comprising a confocal mirror that receives X-rays radiated from the X-ray tube, reflects a plurality of focused X-ray beams monochromatized at a specific wavelength, and focuses the plurality of focused X-ray beams to a preset focal point; and
a slit mechanism that transmits therethrough an arbitrary number of focused X-ray beams out of the plurality of focused X-ray beams reflected from the X-ray optical element.

Furthermore, the X-ray irradiation unit preferably has a configuration for adjusting rotation of the X-ray optical element around a center axis of the plurality of focused X-ray beams reflected from the X-ray optical element.

The slit mechanism is preferably provided with two shielding plates formed of a material for shielding X-rays, and configured to pass the arbitrary number of focused X-ray beams through a gap formed between the shielding plates, and has a function of freely adjusting the extent of the gap.

The X-ray optical element may be configured to reflect four rectangular focused X-ray beams at four corners of a virtual rectangle when viewed in optical path directions of X-rays reflected from the X-ray optical element.

A bundle of the four focused X-ray beams as described above has a large X-ray intensity, and is suitable for fluorescence X-ray measurement.

In this configuration, with respect to two focused X-ray beams passing through the gap of the shielding plates out of the four focused X-ray beams reflected from the X-ray optical element, positional relationship of optical paths of the two focused X-ray beams is preferably adjusted so as to make the two focused X-ray beams incident to an inspection target face of the inspection target so that a virtual plane containing the two focused X-ray beams is parallel to the inspection target face when viewed in the directions of the optical paths of the two focused X-ray beams.

The focused X-ray beams as described above are small in spreading in the height direction, and suitable for X-ray reflectivity measurement.

The slit mechanism may be configured to pass only one of the four focused X-ray beams reflected from the X-ray optical element through the gap of the shielding plates.

The focused X-ray beams as described above are small in spreading in the height direction and the width direction, and suitable for X-ray reflectivity measurement for a minute pattern formed on a semiconductor wafer as an inspection target.

The X-ray irradiation unit may comprise:

an X-ray tube that radiates X-rays; and an X-ray optical element that is configured so that a double curved monochromator crystal plate comprising a semiconductor single crystal plate with a reflection surface having a high-order curved surface of a tertiary or higher order curved surface is fixed to a support block, makes X-rays radiated from the X-ray tube incident to the reflection surface and reflects focused X-rays monochromatized at a specific wavelength.

In this configuration, the X-ray optical element is preferably configured to be curved in a length direction thereof for setting of an X-ray acceptance angle, and also curved in a width direction perpendicular to the length direction for setting of the X-ray acceptance angle.

The focused X-rays emitted from the thus-configured X-ray irradiation unit have large intensities and are suitable for fluorescence X-ray measurement.

The respective X-ray irradiation units having different structures described above may be installed on the first rotation member of the goniometer to be arranged in juxtaposition with each other in a rotation direction.

By using one focused X-ray beam passing through the gap of the shielding plates out of the four focused X-ray beams reflected from the X-rayoptical element, a one-dimensional X-ray detector may be installed on the second rotation member to acquire detection data of X-rays according to a TDI system and perform an X-ray reflectivity measurement.

The whole range of X-rays reflected from a thin film sample as the inspection target can be received by the one-dimensional X-ray detector without receiving slit.

Here, reflected X-rays that are at least totally reflected from the thin film sample can be received by the one-dimensional X-ray detector while the intensity thereof is attenuated by an X-ray absorption member.

Furthermore, an X-ray shielding member may be arranged at a position opposite to a focusing position of incident X-rays to the surface of the thin film sample or an emission position of reflected X-rays so as to form a gap through which incident X-rays incident to the thin film sample or reflected X-rays from the thin film sample can pass. Still furthermore, a receiving slit may be arranged in an optical path of reflected X-rays from the thin film sample so as to form a gap through which the reflected X-rays can pass.

Accordingly, scattered X-rays from air, ghost from a reflection mirror, etc. can be shielded by the X-ray shielding member or the receiving slit, and incidence of these X-rays other than the reflected X-rays to the one-dimensional X-ray detector can be suppressed, whereby the background (BG) components can be reduced.

DESCRIPTION OF REFERENCE NUMERALS

10: sample stage, 20: positioning mechanism, 30: goniometer, 31: goniometer main body, 32: first rotation arm, 33: second rotation arm, 40: X-ray irradiation unit, 41: tube shield, 41a: first tube, 41b: second tube, 42: X-ray tube, 43: X-ray optical element, 46: slit mechanism, 46a: shielding plate, 46b: shielding plate, 50: X-ray detector, 51: one-dimensional X-ray detector, 52: X-ray absorption member, 53: X-ray shielding member, 54: receiving slit, 60: fluorescence X-ray detector, 70: optical microscope, 100: central processing unit, 110: temperature measuring unit

BEST MODES FOR CARRYING OUT THE INVENTION

Embodiments according to the present invention will be described hereunder in detail with reference to the drawings.

[Basic Configuration of X-Ray Thin Film Inspection Device]

Figure 1:
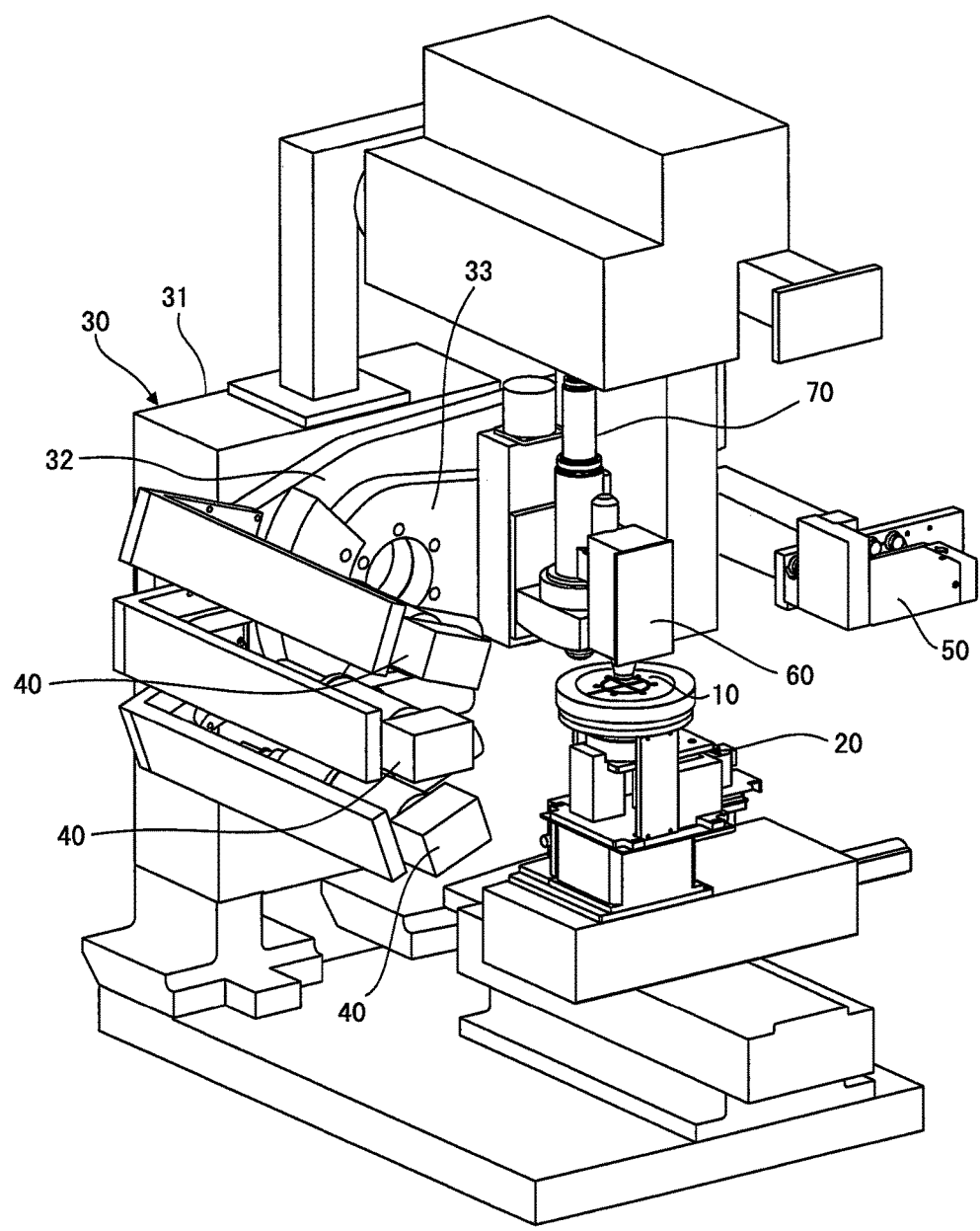
FIG. 1 is a perspective view showing the overall structure of an X-ray thin film inspection device according to an embodiment of the present invention.
Figure 2:
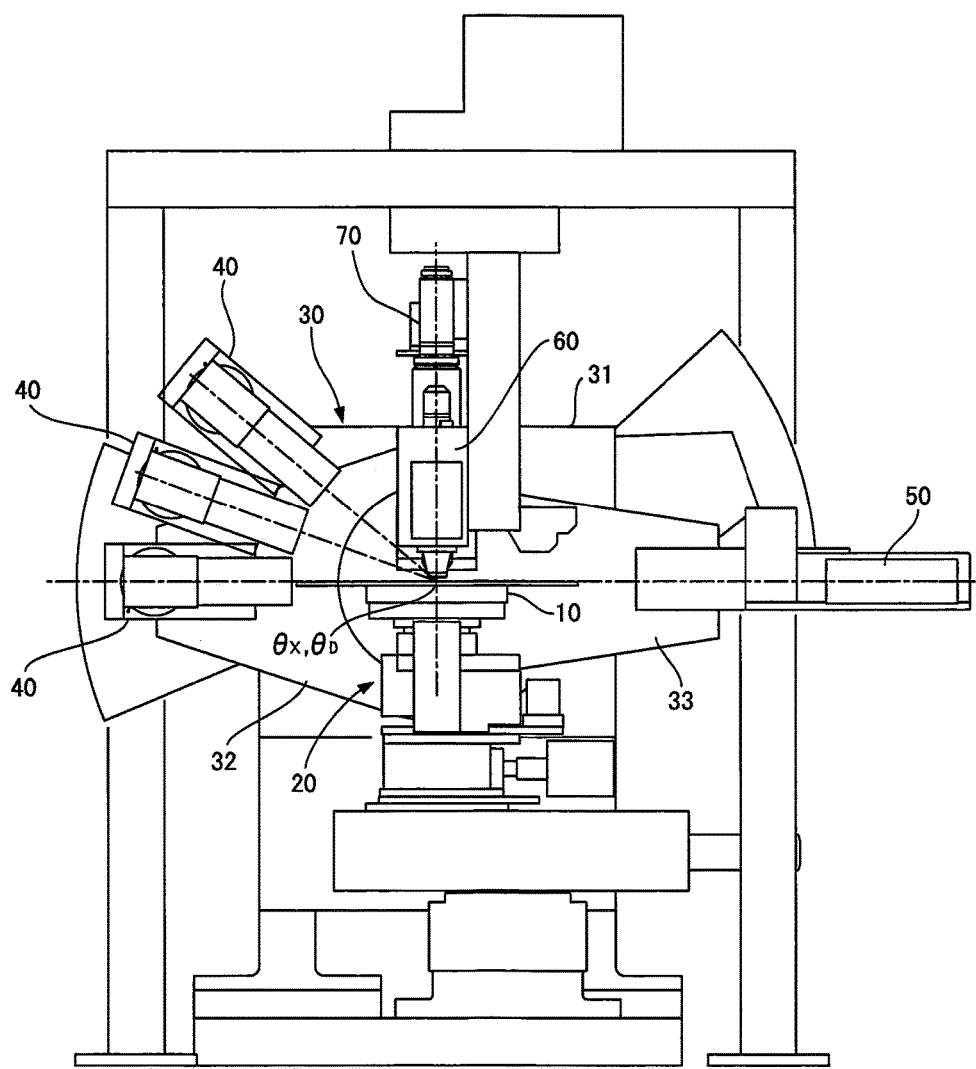
FIG. 2 is a front view showing the overall structure of the X-ray thin film inspection device according to the embodiment of the present invention.

FIG. 1 is a perspective view showing the overall configuration of an X-ray thin film inspection device according to an embodiment, and FIG. 2 is a front view of the device.

The X-ray thin film inspection device includes a sample stage 10, a positioning mechanism 20, a goniometer 30, an X-ray irradiation unit 40, an X-ray detector 50, a fluorescence X-ray detector 60, and an optical microscope 70 (image observing unit) comprising a CCD camera or the like.

A semiconductor wafer as an inspection target is disposed on the upper surface of the sample stage 10, and the sample stage 10 is driven by a positioning mechanism 20. The positioning mechanism 20 has a horizontal movement mechanism which is freely movable in two orthogonal directions (X and Y directions) within a horizontal plane, an elevating mechanism which is freely movable in a up-and-down direction (Z-direction) perpendicular to the horizontal plane, and an in-plane rotating mechanism. The positioning mechanism 20 has a function of moving the sample stage 10 in the X, Y and Z directions and also rotating the sample stage 10 within a plane, whereby any site-under-measurement of the semiconductor wafer disposed on the upper surface of the sample stage 10 is positioned at a focusing position of irradiated X-ray while set in a predetermined oriented state.

The goniometer 30 includes a goniometer main body 31, and first and second rotation arms (rotation members) 32, 33 installed in the goniometer main body 31. Each of the rotation arms 32, 33 rotates along a virtual plane perpendicular to the upper surface of the sample stage around an axis ($\theta_X$-axis, $\theta_D$-axis) vertical to the paper surface of FIG. 2. Here, when the rotation angle of the first rotation arm 32 from the horizontal position thereof is represented by $\theta_X$ and the rotation angle of the second rotation arm 33 from the horizontal position thereof is represented by $\theta_D$.

A plurality of (three in the figures) X-ray irradiation units 40 are installed on the first rotation arm 32 rotating around the $\theta_X$-axis so as to be arranged in juxtaposition with one another in the rotation direction. An X-ray detector 50 is installed on the second rotation arm 33 rotating around the $\theta_D$-axis.

The number of X-ray irradiation units 40 to be installed on the first rotation arm 32 may be set to any number depending on the intended use. For example, the device may be configured so that one, two or four or more X-ray irradiation units 40 are installed on the first rotation arm 32.

The X-ray irradiation unit 40 has a function of monochromatizing X-rays generated from the X-ray tube into X-rays of a specific wavelength, and also focusing the X-rays on one place.

A position to which X-rays from the X-ray irradiation unit 40 are irradiated is an inspection position, and a site-under-measurement of an inspection target disposed on the upper surface of the sample stage 10 is positioned at this inspection position by the positioning mechanism 20.

The details of the X-ray irradiation unit 40 will be described later.

The X-ray detector 50 is used for X-ray reflectivity measurement (XRR) and X-ray diffraction measurement (XRD), and the fluorescence X-ray detector 60 is used for fluorescence X-ray measurement (XRF). According to the X-ray reflectivity measurement, the measurement precision of an angstrom order in film thickness is achieved because interference between reflected X-rays on the film surface and reflected X-rays at the interface between the film and the substrate is measured to derive film thickness and density. Furthermore, according to the fluorescence X-ray measurement, relatively thick wiring film can be measured with high precision. The X-ray thin film inspection device according to this embodiment is configured to be capable of performing the X-ray diffraction measurement as required in addition to the X-ray reflectivity measurement and the fluorescence X-ray measurement.

For example, an avalanche photodiode (APD) having a broad dynamic range to incident X-rays may be used as the X-ray detector 50.

The device may be configured so that a detector exchanging mechanism is incorporated into the second rotation arm 33, and various kinds of X-ray detectors such as APD, a one-dimensional X-ray detector, a two-dimensional detector, a scintillation counter, etc. are mounted and allowed to be used while switching these X-ray detectors to one another by the detector exchanging mechanism.

Furthermore, the fluorescence X-ray detector 60 is arranged at an upper position of the aforementioned inspection position, and the optical microscope 70 is arranged to be horizontally displaced from the inspection position by only $L_P$, thereby avoiding interference with the fluorescence X-ray detector 60.

The site-under-measurement of the inspection target (for example, a semiconductor wafer) disposed on the sample stage 10 is located at a lower position of the optical microscope 70 by moving the sample stage 10 with the positioning mechanism 20. Furthermore, the site-under-measurement is horizontally moved from this position to the inspection position by only $L_P$, whereby the site-under-measurement of the inspection target (for example, the semiconductor wafer) is positioned at the inspection position.

The device may be configured so that an equipment exchanging mechanism is provided above the sample stage 10, and any one of the fluorescence X-ray detector 60 and the optical microscope 70 is selected by the equipment exchanging mechanism and arranged at an upper position of the inspection position.

According to the X-ray thin film inspection device having the aforementioned basic configuration, the plural (three in FIGS. 1 and 2) X-ray irradiation units 40 are installed on the first rotation arm 32 so as to be arranged in juxtaposition with one another in the rotation direction, whereby plural X-ray irradiation units 40 are selected and a selected X-ray irradiation unit can be positioned at a measurement position at any angle with high precision by only rotating the first rotation arm 32.

For example, when the X-ray reflectivity measurement is performed by this device, an X-ray irradiation unit 40 for generating desired X-rays is selected, and the selected X-ray irradiation unit 40 may be arranged so that X-rays are irradiated to a semiconductor wafer as a measurement target at a low angle so as to be incident very closely to the surface of the semiconductor wafer. When a normal X-ray diffraction measurement is performed, the position of the selected X-ray irradiation unit 40 is sequentially moved to appropriately change the incident angle of X-rays to the semiconductor wafer. Furthermore, when the fluorescence X-ray measurement is performed, the selected X-ray irradiation unit 40 may be arranged so as to irradiate the measurement target with X-rays at a low angle.

According to the X-ray thin film inspection device of this embodiment, the selection and positioning of the these X-ray irradiation units 40 can be performed with high precision by only rotating the first rotation arm 32.

In the X-ray reflectivity measurement, it is possible to derive the film thickness, density and roughness of not only a monolayer film, but also each layer of several underlayers from the surface. In addition, since the plural X-ray irradiation units 40 are enabled to be installed on the first rotation arm 32, higher-precision multilayer analysis using X-rays having plural different wavelengths can be performed.

In the fluorescence X-ray measurement, an X-ray irradiation unit 40 for generating X-rays of a wavelength suitable for the fluorescence X-ray measurement is selected according to an inspection target (for example, semiconductor wafer), and the first rotation arm 32 rotates to arrange the selected X-ray irradiation unit at an incident angle position at which the incident angle of X-rays from the selected X-ray irradiation unit to the inspection target is low.

A margin space in which incident X-rays to the inspection target are not shielded by the fluorescence X-ray detector 60 can be formed by setting the incident angle to a low angle as described above, and the fluorescence X-ray detector 60 is moved downwards by a vertically moving mechanism incorporated in the equipment exchanging mechanism 80, whereby the fluorescence X-ray detector 60 can be arranged in proximity to the surface of the inspection target as compared with a case where other elements are measured.

Accordingly, an X-ray path (an incident space of X-rays) between the measurement face of the inspection target and the fluorescence X-ray detector 60 can be configured as a minute space, and most of fluorescence X-rays generated from the measurement face of the inspection target can be captured by the fluorescence X-ray detector 60 before absorbed by air.

Figure 3:
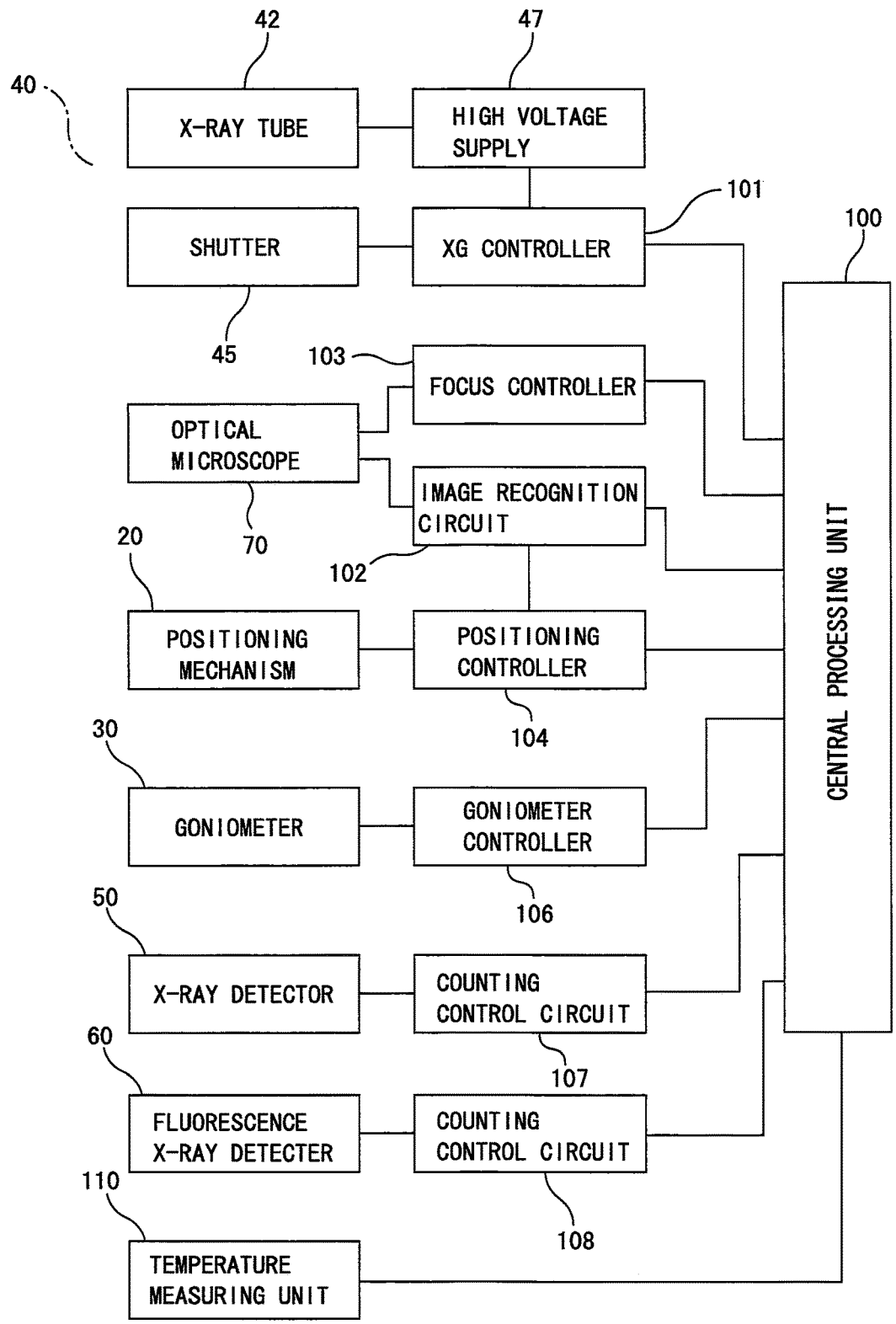
FIG. 3 is a block diagram showing a control system for the X-ray thin film inspection device according to the embodiment of the present invention.

FIG. 3 is a block diagram showing a control system for the X-ray thin film inspection device according to the embodiment.

An XG controller 101 executes supply of a high voltage power supply 47 to the X-ray tube 42 incorporated in the X-ray irradiation unit 40 and the opening/closing operation of a shutter 45. An image captured by the optical microscope 70 is subjected to pattern recognition in an pattern recognition circuit 102. The focal position of the optical microscope 70 is adjusted by a focus controller 103. A positioning controller 104 controls the operation of the positioning mechanism 20 based on image information which is captured by the optical microscope and subjected to the pattern recognition by the pattern recognition circuit 102. The goniometer 30 is controlled by a goniometer controller 106.

The XG controller 101, the pattern recognition circuit 102, the focus controller 103, the positioning controller 104 and the goniometer controller 106 are respectively operated based on setting information from a central processing unit (CPU) 100. The X-ray detector 50 and the fluorescence X-ray detector 60 are controlled by counting control circuits 107 and 108, respectively. These controllers, CPU, the counting control circuits constitute control means of the X-ray thin film inspection device.

Figure 4:
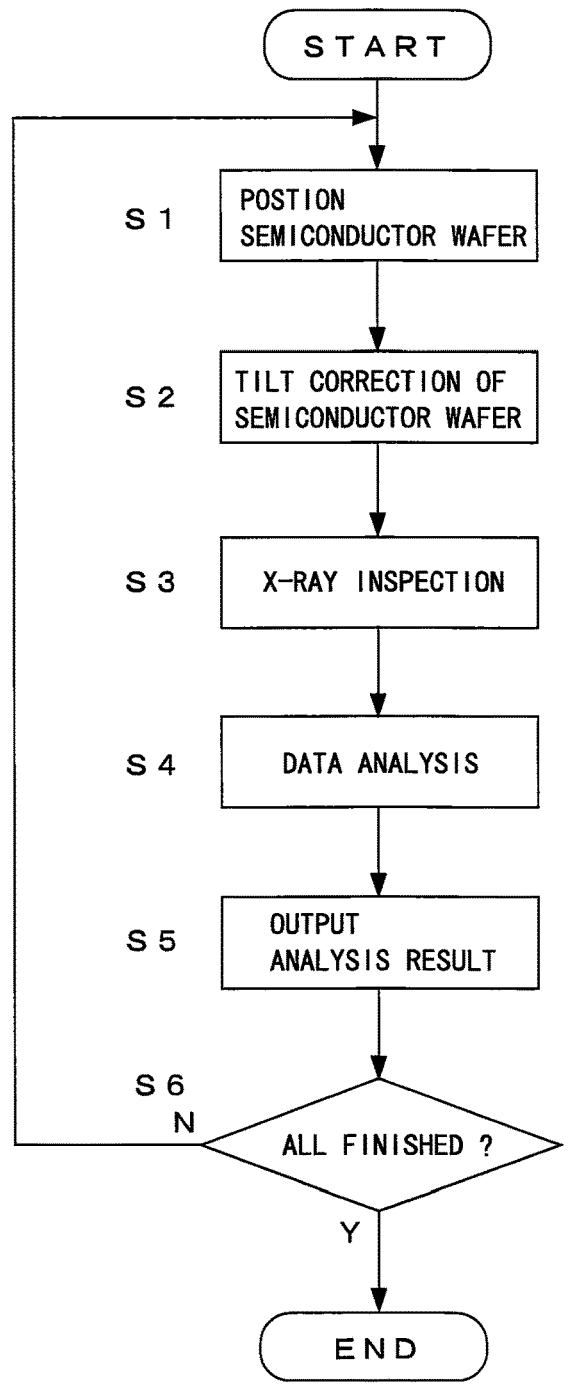
FIG. 4 is a control flowchart showing the X-ray thin film inspection device according to the embodiment of the present invention.

FIG. 4 is a control flowchart when an X-ray thin film inspection for a semiconductor wafer as an inspection target is executed.

After a semiconductor wafer as an inspection target is disposed on the sample stage 10, a site-under-measurement of the semiconductor wafer is first positioned at the inspection position (step S1). This positioning is executed by controlling of the driving of the positioning mechanism 20. That is, the optical microscope 70 captures the semiconductor wafer on the sample stage 10, and the positioning controller 104 controls the driving of the positioning mechanism 20 based on image information recognized by the pattern recognition circuit 102. The positioning mechanism 20 moves in the horizontal two directions (X-Y directions) and the height direction (Z-direction) to set the site-under-measurement of the semiconductor wafer at the inspection position.

When a minute thin film pattern within a semiconductor element formed on a semiconductor wafer is set as the site-under-measurement, a minute pattern of a positioning pattern, a scribe line of the semiconductor element, a memory portion, a dummy pattern, a specific site of an IC chip, etc. formed on the semiconductor wafer as an inspection target is pre-stored in the pattern recognition circuit 102, an inspection target area of the semiconductor wafer as an inspection target is observed by the optical microscope 70 when an inspection is performed, and the observed image and the pre-stored minute pattern are compared and matched with each other, whereby the pattern recognition circuit 102 determines whether the inspection target area is the minute pattern as the site-under-measurement. On the basis of the determination result, the positioning mechanism 20 positions the minute pattern as the site-under-measurement at a position under measurement.

Furthermore, when the minute pattern within the semiconductor element formed on the semiconductor wafer is set as a site-under-measurement as described above, it is preferable that the longitudinal direction thereof is set to be matched with the incident direction of X-rays. This direction matching can be performed at a short movement distance through the movement in the horizontal two directions (X-Y directions) and the in-plane rotation by the positioning mechanism 20.

Figure 5:
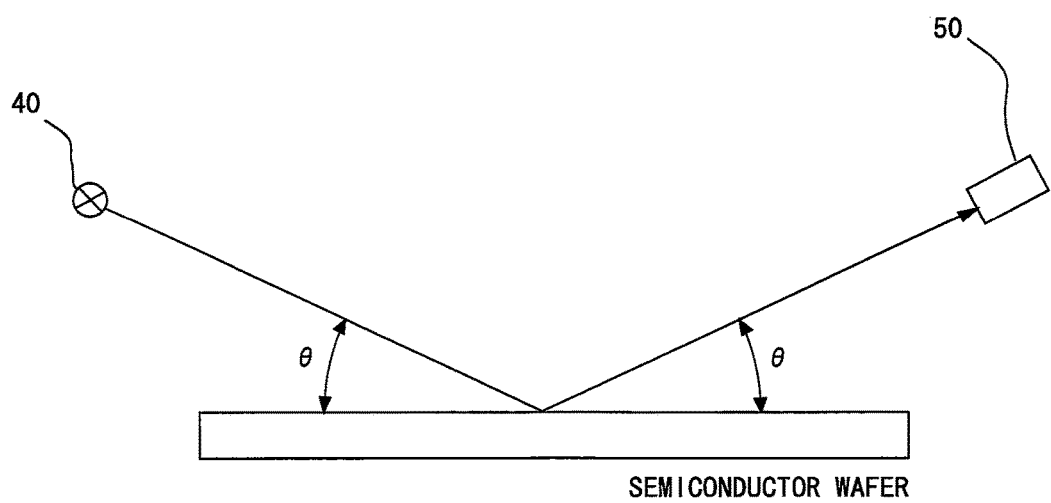
FIG. 5 is a schematic diagram showing tilt correction of a semiconductor wafer.

Next, tilt correction of the semiconductor wafer is performed (step S2). This tilt correction is performed by rotating the first and second rotation arms 32 and 33 of the goniometer 30 while the semiconductor wafer is fixed as shown in FIG. 5. When the incident angle of X-rays from the X-ray irradiation unit 40 to the semiconductor wafer is represented by θ, X-rays are reflected from the surface of the semiconductor wafer at an angle of θ. The reflected X-rays are detected by the X-ray detector 50. Accordingly, the X-ray irradiation unit 40 and the X-ray detector 50 are arranged at the same angular positions with respect to the surface of the semiconductor wafer, and the angle control of each of the X-ray irradiation unit 40 and the X-ray detector 50 can be performed with respect to the above angular position as an origin.

After the site-under-measurement of the semiconductor wafer is positioned and the tilt correction is performed as described above, the X-ray inspection is performed by using any one of the X-ray reflectivity measurement (XRR), the fluorescence X-ray measurement (XRF) and the X-ray diffraction measurement (XRD) (step S3), inspection data are analyzed by the central processing unit (step S4), and an analysis result is output (step S5).

Each of the aforementioned steps is performed on all site-under-measurements which are set in the semiconductor wafer (step S6), and finished after the inspection of all the site-under-measurements is completed.

When the throughput is prioritized in the fluorescence X-ray measurement (XRF) at a low angle or the X-ray reflectivity measurement (XRR), the aforementioned tilt correction of the semiconductor wafer (step S2) may be omitted. Furthermore, the tilt correction of the semiconductor wafer (step S2) is normally omitted in the fluorescence X-ray measurement (XRF) at angles other than the low angle.

[X-Ray Irradiation Unit (Part 1)]

Next, a first embodiment according to the X-ray irradiation unit 40 will be described in detail with reference to FIGS. 6 to 15.

Figure 6:
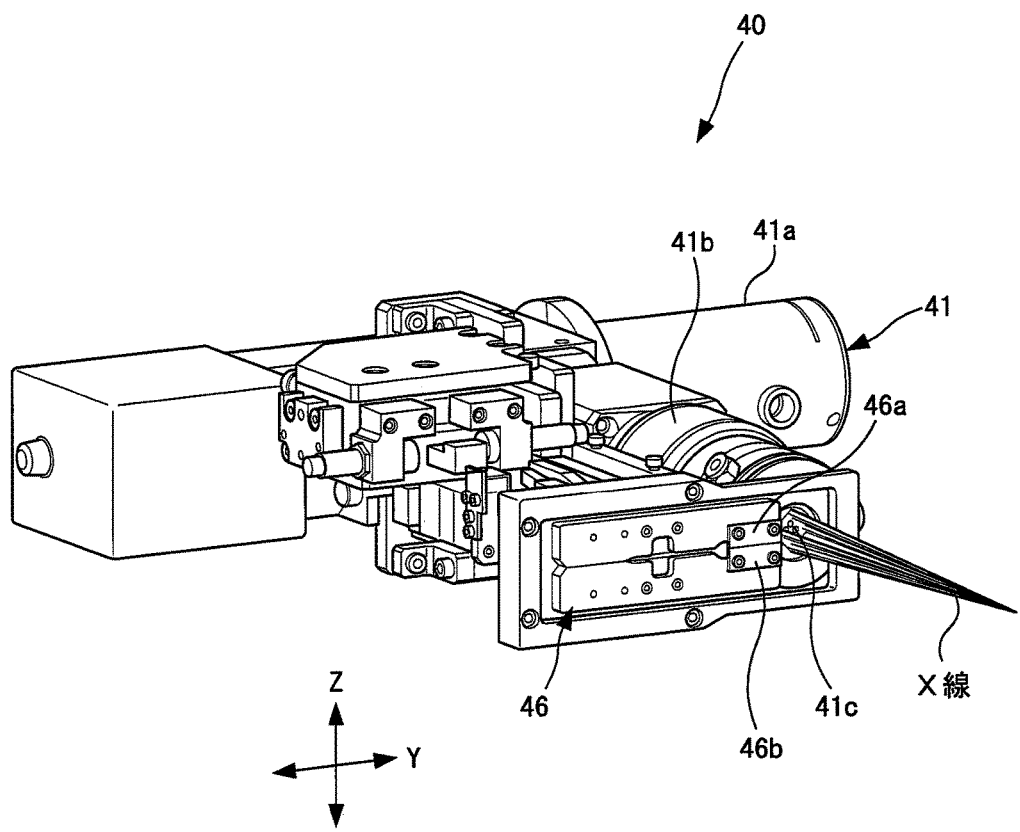
FIG. 6 is a perspective view showing the appearance of a first embodiment of an X-ray irradiation unit.
Figure 7:
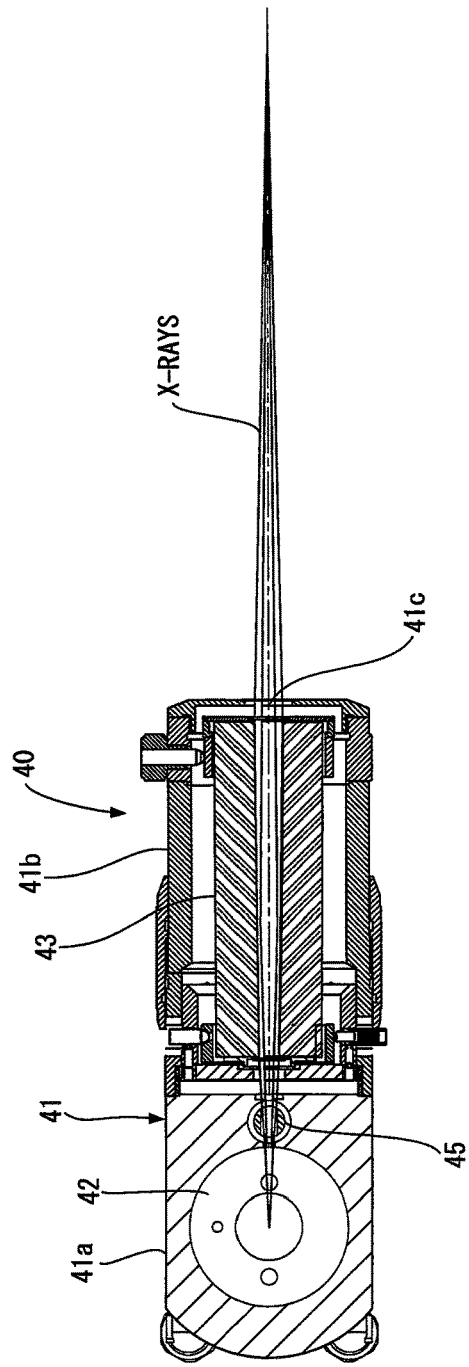
FIG. 7 is a longitudinally-sectional view of the first embodiment of the X-ray irradiation unit.
Figure 8:
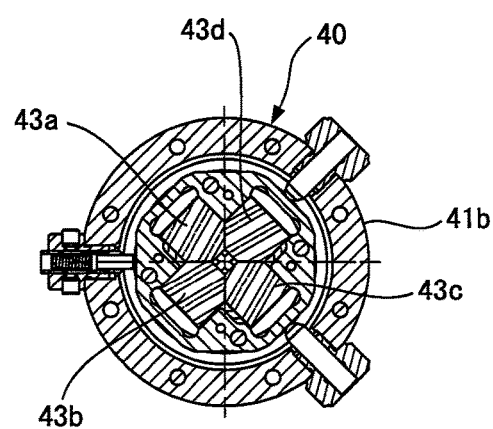
FIG. 8 is a cross-sectional view of the first embodiment of the X-rays irradiation unit.

The X-ray irradiation unit 40 has an external appearance as shown in FIG. 6, and it can perform downsizing and lightening as a module configuration having an X-ray tube 42 as an X-ray source and an X-ray optical element 43 incorporated in a tube shield (unit main body) 41 as shown in FIGS. 7 and 8. The tube shield 41 is formed of a metal material for shielding X-rays, and divided into a first tube 41*a* containing the X-ray tube 42 therein and a second tube 41*b* containing the X-ray optical element 43 therein. The tubes 41*a* and 41*b* are joined and unified into one body by fastening means such as a bolt or the like.

As shown in FIG. 7, an X-ray path for leading X-rays radiated from the X-ray tube 42 to an X-ray emission port 41*c* is formed in the tube shield 41, and a shutter 45 for opening/closing the X-ray path is arranged in the first tube 41*a*. The shutter 45 is configured to open or close by its rotation so as to pass or shield X-rays radiated from the X-ray tube 42.

As the X-ray tube 42 may be used, for example, a microfocus X-ray tube which has an electron beam focal point size of about ϕ30 μm on a target and output power of about 30 W. Any material such as copper (Cu), molybdenum (Mo) or the like may be selected as the material of the target as required. Other materials such as iron (Fe), cobalt (Co), tungsten (W), chromium (Cr), silver (Ag), gold (Au), etc. may be used. For example, plural X-ray irradiation units 40 in which X-ray tubes 42 of different target materials are incorporated may be installed on the first rotation arm 32.

A confocal mirror for focusing X-rays generated from the X-ray tube 42 on a predetermined position is used as the X-ray optical element 43. The confocal mirror comprises four multilayer mirrors 43*a*, 43*b*, 43*c* and 43*d* as shown in FIG. 8. Each of the multilayer mirrors 43*a*, 43*b*, 43*c* and 43*d* is formed of a multilayer having an elliptical arc surface, and the adjacent multilayer mirrors 43*a* and 43*b* (43*c* and 43*d*) are arranged so that the end edges of the X-ray reflection surfaces thereof cross each other at an angle of about 90°.

The X-ray optical element 43 comprising this confocal mirror can focus X-rays generated in the X-ray tube 42 on a minute focal point, and monochromatizes the X-rays. For example, in the case of the X-ray tube 42 using a Cu target, the X-rays can be monochromatized to CuKα, and in the case of the X-ray tube 42 using a Mo target, the X-rays can be monochromatized to MoKα. It is preferable that a multilayer mirror may be appropriately selected and used according to the wavelength of X-rays to be monochromatized.

Figure 9:
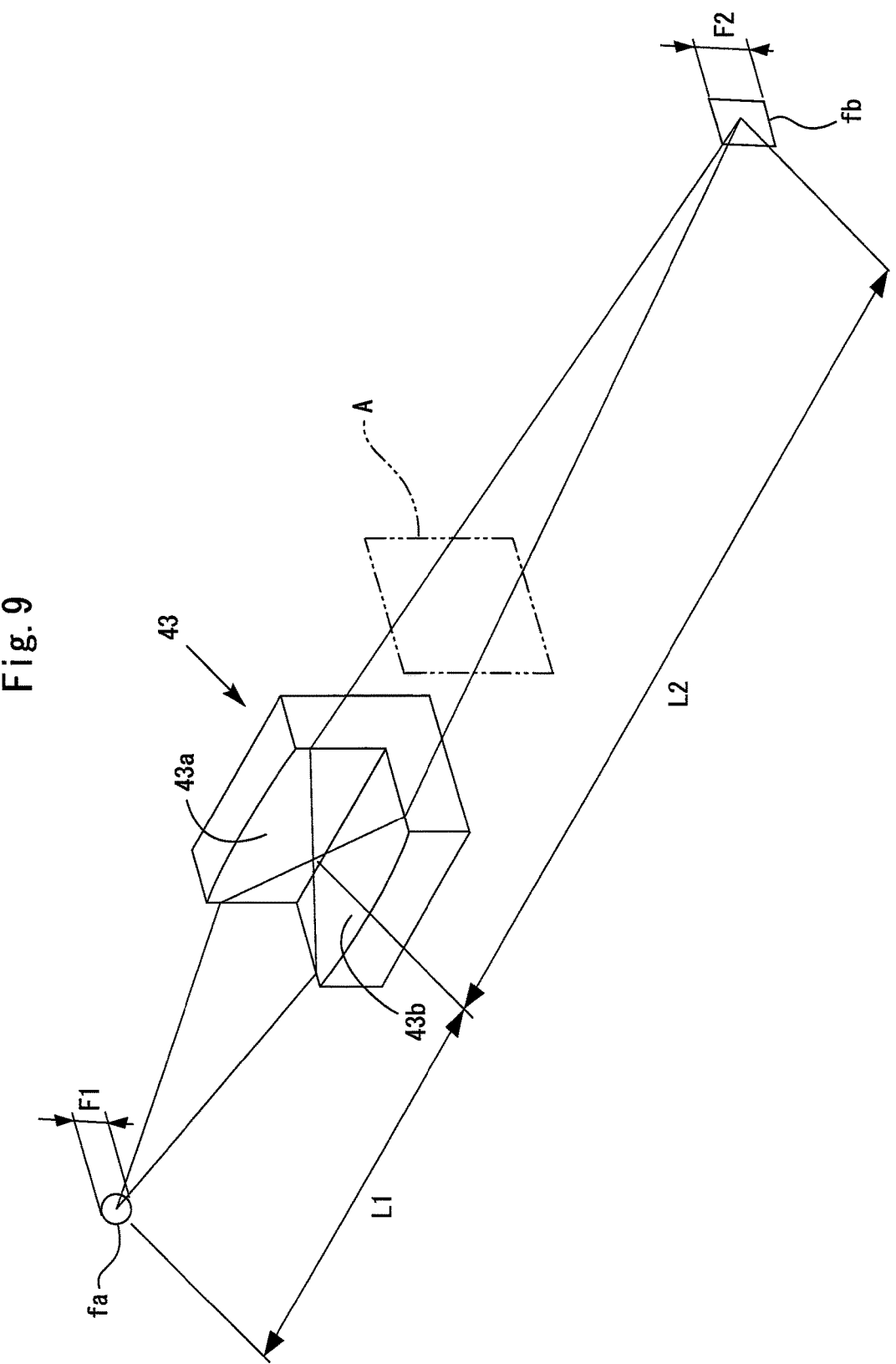
FIG. 9 is a diagram showing a reflection path of X-rays in an X-ray optical element.

FIG. 9 is a diagram showing a reflection path of X-rays in the X-ray optical element (confocal mirror).

Figure 10A:
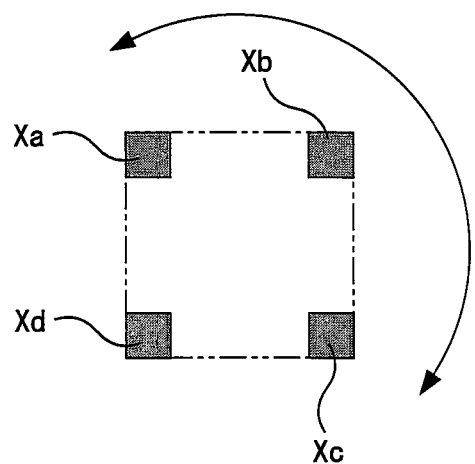
FIGS. 10A and 10B are views of four focused X-ray beams reflected from the X-ray optical element when viewed in an optical path direction.

X-rays incident to the X-ray optical element 43 are reflected between the two adjacent multilayer mirrors 43*a* and 43*b* out of the four multilayer mirrors, and then output as monochromatized focused X-rays. That is, X-rays are first reflected at the first multilayer mirror 43*a*, and further reflected at the second multilayer mirror 43*b*, whereby the X-rays are emitted as focused X-ray beams each having a rectangular cross-sectional shape as shown in FIG. 10A. Furthermore, when X-rays which are first reflected at the second multilayer mirror 43*b* are further reflected at the first multilayer mirror 43*a*, the X-rays are then likewise emitted as focused X-ray beams each having a rectangular cross-sectional shape as shown in FIG. 10A. As not shown, X-rays are likewise reflected between the other two adjacent multilayer mirrors 43*c* and 43*d*, and then emitted as focused X-ray beams each having a rectangular cross-sectional shape as shown in FIG. 10A.

Accordingly, four focused X-ray beams Xa, Xb, Xc and Xd each having a rectangular shape are emitted from the X-ray optical element 43 to four corners of a virtual rectangle as shown in FIG. 10A.

The cross-sectional shapes of the focused X-ray beams Xa, Xb, Xc and Xd shown in FIG. 10A correspond to cross-sectional shapes taken along a cutting plane A at an intermediate position of an X-ray path of the X-rays reflecting from the X-ray optical element 43 and reaching the focusing position fb as shown in FIG. 9. At the focusing position fb, the respective focused X-ray beams Xa, Xb, Xc and Xd are superposed into a single X-ray beam.

Accordingly, when the four focused X-ray beams Xa, Xb, Xc and Xd are superposed into a single X-ray beam at the focusing position fb, the X-ray intensity which is four times as large as the intensity of one focused X-ray beam can be obtained. As described later, when the two focused X-ray beams Xb and Xd are superposed into a single X-ray beam at the focusing position fb, the X-ray intensity which is twice as large as the intensity of one focused X-ray beam can be obtained.

The focusing position fb of the focused X-ray beams Xa, Xb, Xc and Xd shown in FIG. 9 is matched with the measurement position of the semiconductor wafer, and any site-under-measurement in the semiconductor wafer is positioned at the focusing position fb by the aforementioned positioning mechanism 20. The measurement position is set on the θ-axis of the goniometer 30.

Here, when the focal point size (length) of an electron beam in the X-ray tube 42 is represented by F1, the distance from the focal point fa of the X-ray tube 42 to the reflection center position of the X-ray optical element 43 is represented by L1, and the distance from the reflection center position of the X-ray optical element 43 to the focusing position fb of the focused X-rays is represented by L2 as shown in FIG. 9, the focal point size (length) F2 of the focused X-rays is represented by the following formula: F2=F1(L2/L1).

Accordingly, in order to reduce the focal point size F2 of the focused X-rays, it is preferable that the distance L1 from the focal point fa of the X-ray tube 42 to the reflection center position of the X-ray optical element 43 is set to be as long as possible. A method of shortening the distance L2 from the reflection center position of the X-ray optical element 43 to the focusing position fb of the focused X-rays is difficult because there is a constraint such as interference in the semiconductor wafer or the like.

The second tube 41b of the X-ray optical element 43 is configured to be freely rotatably adjustable relatively to the first tube 41a. For example, when the second tube 41b is rotated by 45° and fixed under this rotated state, the circumferential positions of the respective multilayer mirrors 43a, 43b, 43c and 43d of the X-ray optical element 43 incorporated in the second tube 41b can be rotationally shifted by 45°. As described above, the circumferential positions of the respective multilayer mirrors 43a, 43b, 43c and 43d are rotationally shifted by 45°, whereby the paths of the focused X-rays Xa, Xb, Xc and Xd reflected from the X-ray optical element 43 can be changed from the positions of FIG. 10 to positions of FIG. 10B.

Figure 11:
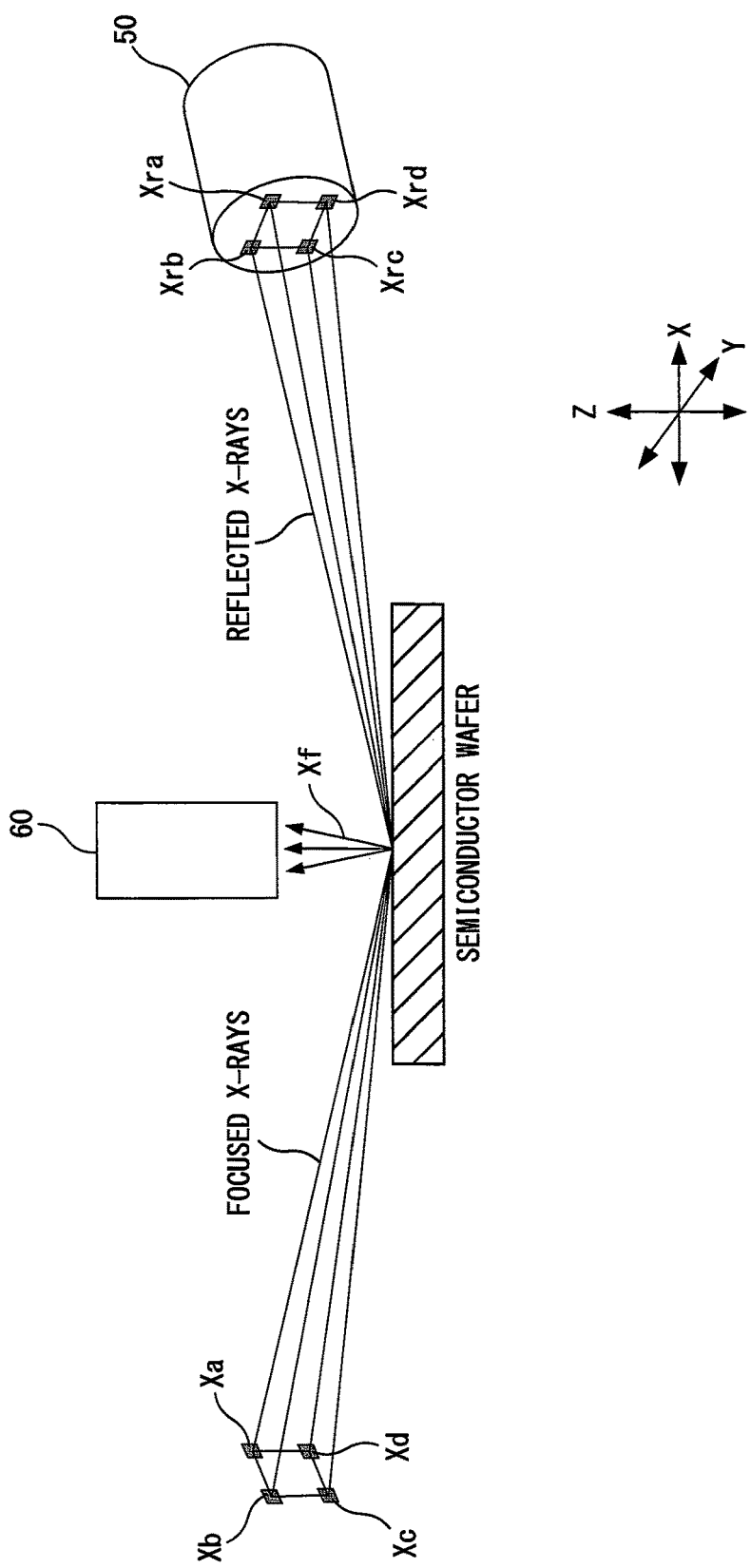
FIG. 11 is a schematic diagram showing the paths of the four focused X-ray beams which are irradiated from the X-ray irradiation unit to an inspection face of a semiconductor wafer, and the paths of divergent X-rays which are reflected from the inspection face and incident to an X-ray detector.

As described above, when the four focused X-ray beams Xa, Xb, Xc and Xd are superposed into a single X-ray beam at the focusing position fb, the X-ray intensity which is four times as large as the intensity of one focused X-ray beam can be obtained. However, when the four focused X-ray beams Xa, Xb, Xc, and Xd as shown in FIG. 10A are irradiated to an inspection target face of a semiconductor wafer, reflected X-ray beams Xra, Xrb, Xrc, and Xrd reflected from the inspection target face of the semiconductor wafer are incident to the X-ray detector 50 while spreading as shown in FIG. 11. As described above, when there is a spread in the height direction (Z-direction) among the reflected X-ray beams Xra, Xrb and Xrd, Xrc incident to the X-ray detector 50, it is impossible to obtain a high-precision measurement result particularly in the X-ray reflectivity measurement.

On the other hand, in the fluorescence X-ray measurement, the spreading of the reflected X-ray beams Xra, Xrb, Xrc and Xrd have no effect on the measurement precision because fluorescence X-rays Xf which is excited and emitted from the semiconductor wafer are captured by the fluorescence X-ray detector 60.

Figure 10B:
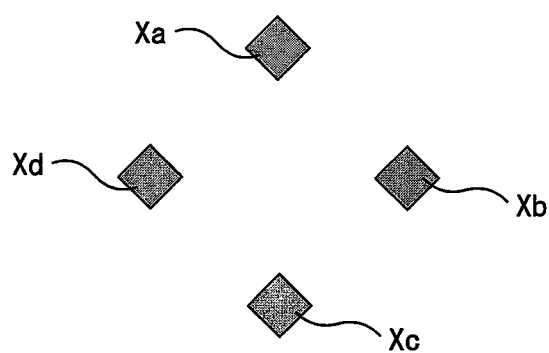

Therefore, in the case of the fluorescence X-ray measurement, the four focused X-ray beams Xa, Xb, Xc, and Xd as shown in FIGS. 10A and 10B are used, and the measurement is performed based on the X-ray intensity which is four times as large as the intensity of one focused X-ray beam, whereby a high-precision measurement result can be obtained. In general, a statistical error out of measurement errors in the X-ray measurement is represented by $\sqrt{N}$ (N represents the X-ray intensity), and the statistical relative error is represented by $\sqrt{N}/N$. When the X-ray intensity increases by four times, the statistical relative error $\sqrt{(4N)}/4N = 1/2 \times \sqrt{N}/N$. That is, by establishing the configuration having the X-ray intensity of four times as described above, the statistical relative error can be halved.

Figure 12:
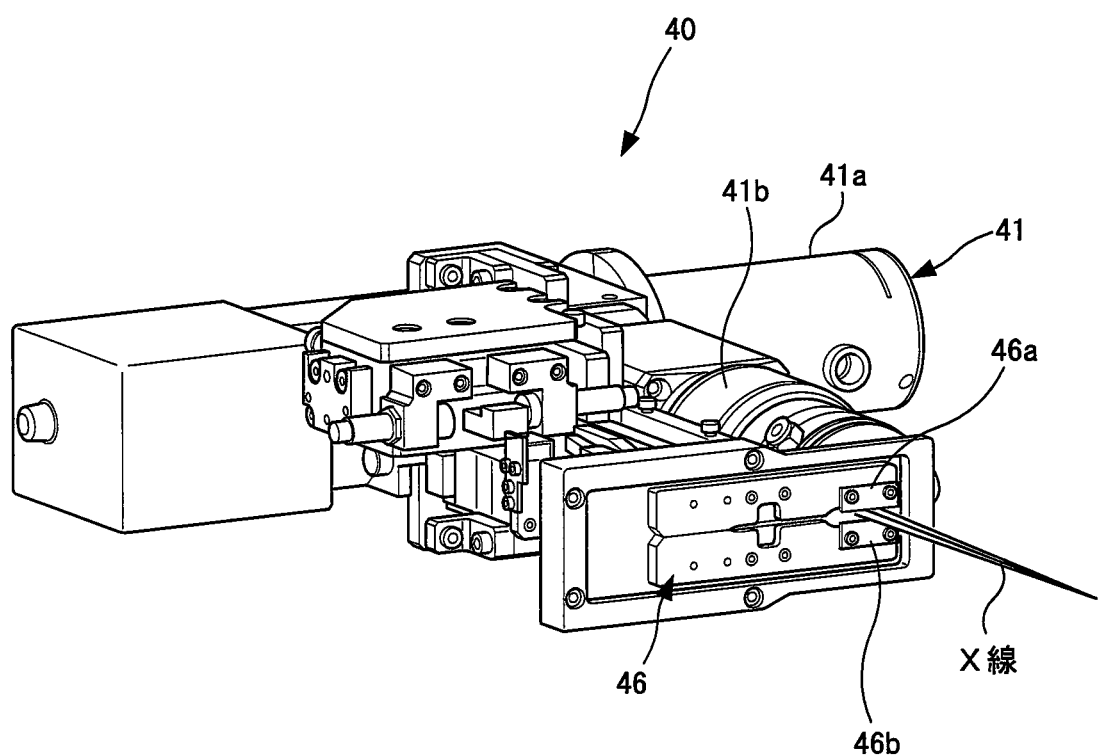
FIG. 12 is a perspective view showing the appearance of the first embodiment according to the X-ray irradiation unit as in the case of FIG. 6.

As shown in FIGS. 6 and 12, the X-ray irradiation unit 40 is provided with a movable slit mechanism 46 that is located in front of the X-ray emission port 41c of the tube shield 41 and shields a part of emitted X-rays. The slit mechanism is incorporated with two shielding plates 46a, 46b which are arranged vertically so as to be freely slidable in the width direction (Y-direction) and the height direction (Z-direction) perpendicular to each other, and these shielding plates 46a, 46b are configured to be positionally changeable by driving force from a driving motor (not shown). Each of the shielding plates 46a, 46b is formed of an X-rays shielding material.

By moving the shielding plates 46a, 46b to an evacuation position shown in FIG. 6, all the four focused X-ray beams Xa, Xb, Xc, and Xd (see FIG. 10) can be emitted from the X-ray emission port 41c.

Figure 13A:
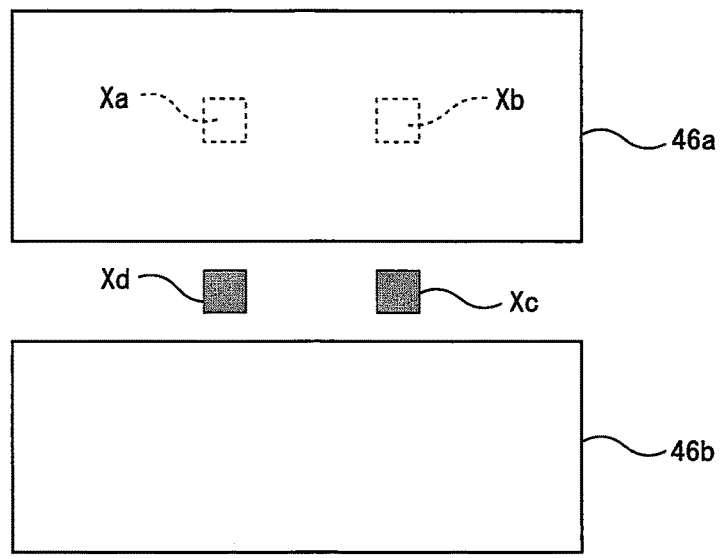
FIGS. 13A and 13B are views of two focused X-ray beams passing through the gap between shielding plates of a slit mechanism when viewed in the optical path direction.
Figure 13B:
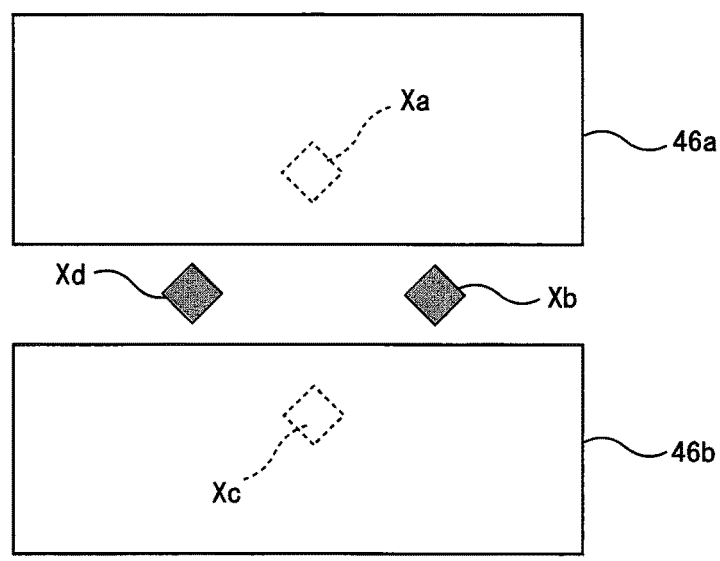

Furthermore, the shielding plates 46a, 46b are moved and arranged to be spaced from each other at a certain interval at a position where some of emitted X-rays are shielded as shown in FIG. 12, whereby two focused X-ray beams Xc and Xd or Xb and Xd can be emitted from the X-ray emission port 41c as shown in FIG. 13A or FIG. 13B, for example.

The shielding plates 46a and 46b described above have the function of a divergence slit (DS: Divergence Slit).

Here, the positional relationship of the optical paths of the two focused X-ray beams Xd and Xc (or Xb, Xd) passing through the gap between the shielding plates 46a and 46b as shown in FIG. 13A or 13B is adjusted so that a virtual plane containing the two focused X-ray beams Xd, Xc (or Xb, Xd) is incident in parallel to the inspection target face of the semiconductor wafer when viewed in the optical path direction of the X-ray beams. The adjustment of the positional relationship can be performed by rotationally adjusting the second tube 41b incorporated with the multilayer mirrors 43a, 43b, 43c and 43d.

Figure 14:
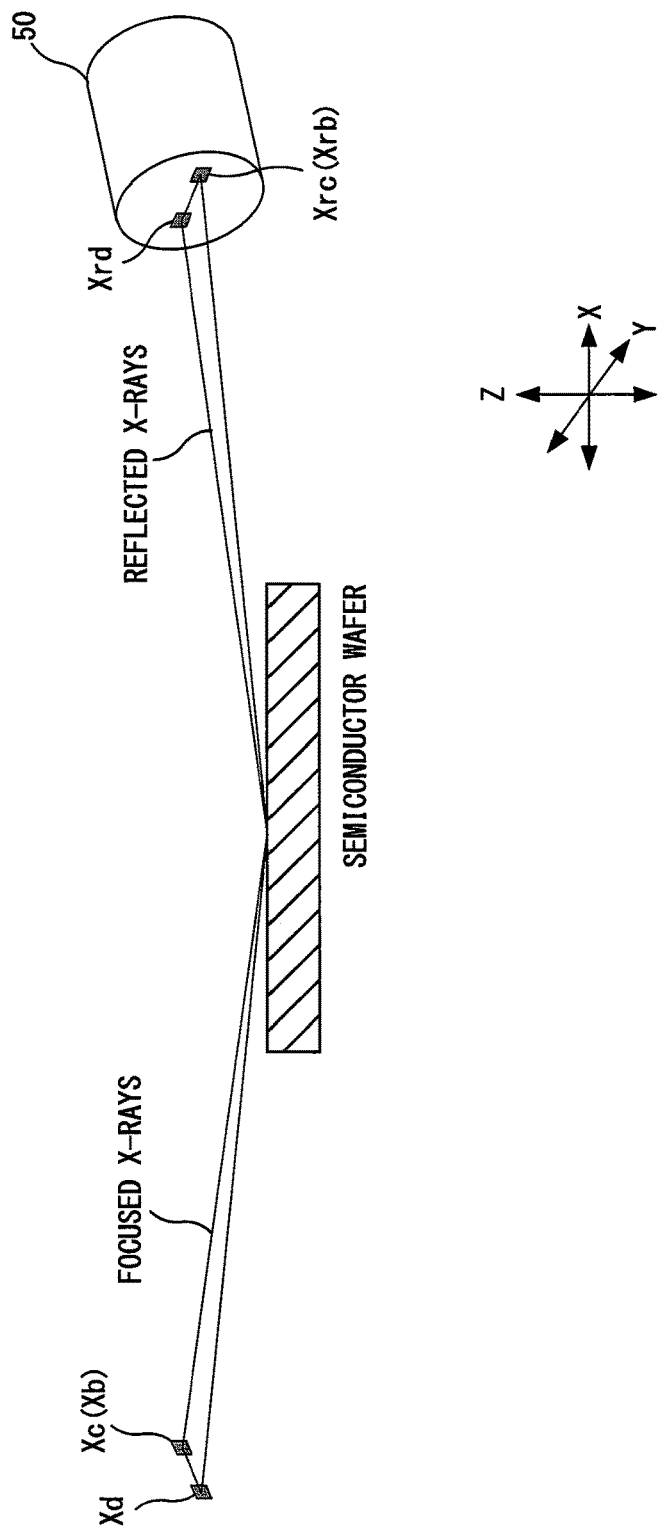
FIG. 14 is a schematic diagram showing the paths of the two focused X-ray beams which are irradiated from the X-ray irradiation unit to the inspection face of the semiconductor wafer, and the paths of divergent X-rays which are reflected from the inspection face and incident to the X-ray detector.

The thus-emitted two focused X-ray beams Xc, Xd or Xb, Xd are suitable for the X-ray reflectivity measurement. That is, when the inspection target face of the semiconductor wafer is irradiated with the two focused X-ray beams Xc, Xd (or Xb, Xd) as shown in FIG. 14, the reflected X-ray beams Xrc, Xrd (or Xrb, Xrd) reflected from the inspection target face of the semiconductor wafer spread in only the width direction (Y-direction), and do not spread in the height direction (Z-direction). Accordingly, these X-ray beams are suitable for the X-ray reflectivity measurement.

Figure 15:
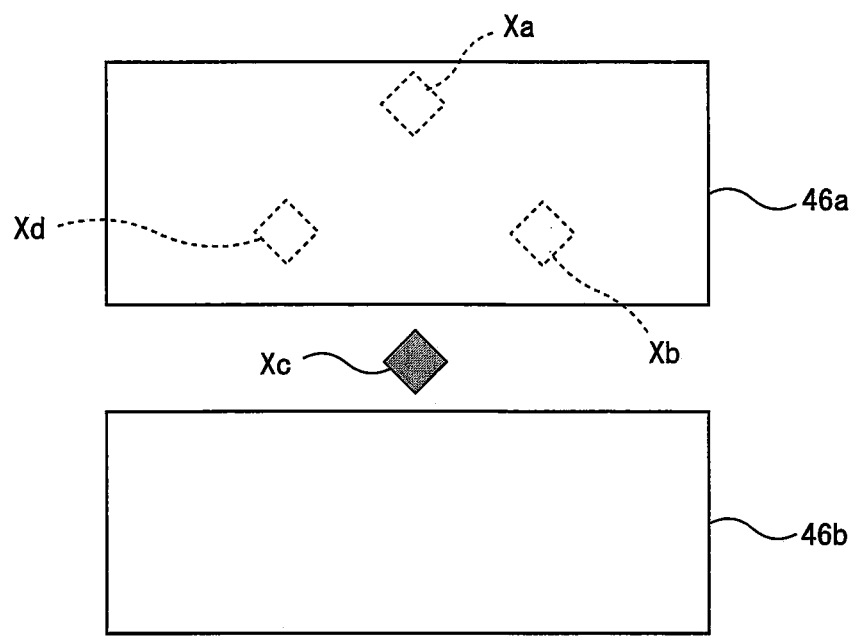
FIG. 15 is a view of one focused X-ray beam passing through the gap between the shielding plates of the slit mechanism when viewed in the optical path direction.

Furthermore, the shielding plates 46a, 46b may be moved and arranged so that only one focused X-ray beam Xc is emitted from the X-ray emission port 41c as shown in FIG. 15. The X-ray intensity is halved as compared with the case where two focused X-ray beams are used, but no spreading occurs in both the width direction (Y-direction) and the height direction (Z-direction). Therefore, this case is also suitable for the X-ray reflectivity measurement.

Although the specific spreading angle of the reflected X-rays varies depending on the design, for example, one X-ray beam has a spreading angle of 0.5°, and two X-ray beams arranged vertically have a spreading angle of 4° therebetween. Four X-ray beams are preferably used for the fluorescence X-ray measurement (XRF). On the other hand, one or two X-ray beams are preferably used for the X-ray reflectivity measurement (XRR). Furthermore, in the X-ray reflectivity measurement (XRR), an X-ray beam may be used while partially shielded by the shielding plates 46a and 46b to limit the beam width thereof within a range from 0.1° to 0.2°. A receiving slit (RS: Receiving Slit) may be provided in front of the X-ray detector to limit the angle, whereby the resolution can be changed in accordance with the inspection target.

As described above, according to the first configuration of the X-ray irradiation unit 40, all the four focused X-ray beams may be used to configure an X-ray source for the fluorescence X-ray measurement, and two or one focused X-ray beam may be used to configure an X-ray source for the X-ray reflectivity measurement. Although the X-ray intensity is reduced as compared with the case where the four focused X-ray beams are used, the fluorescence X-ray measurement may be also performed by using two or one focused X-ray beam.

[X-Ray Irradiation Unit (Part 2)]

Next, a second embodiment of the X-ray irradiation unit 40 will be described in detail with reference to FIGS. 16 to 19.

The X-ray irradiation unit 40 of this embodiment is configured so as to be capable of irradiating large-intensity X-rays suitable for the fluorescence X-ray measurement.

Figure 16:
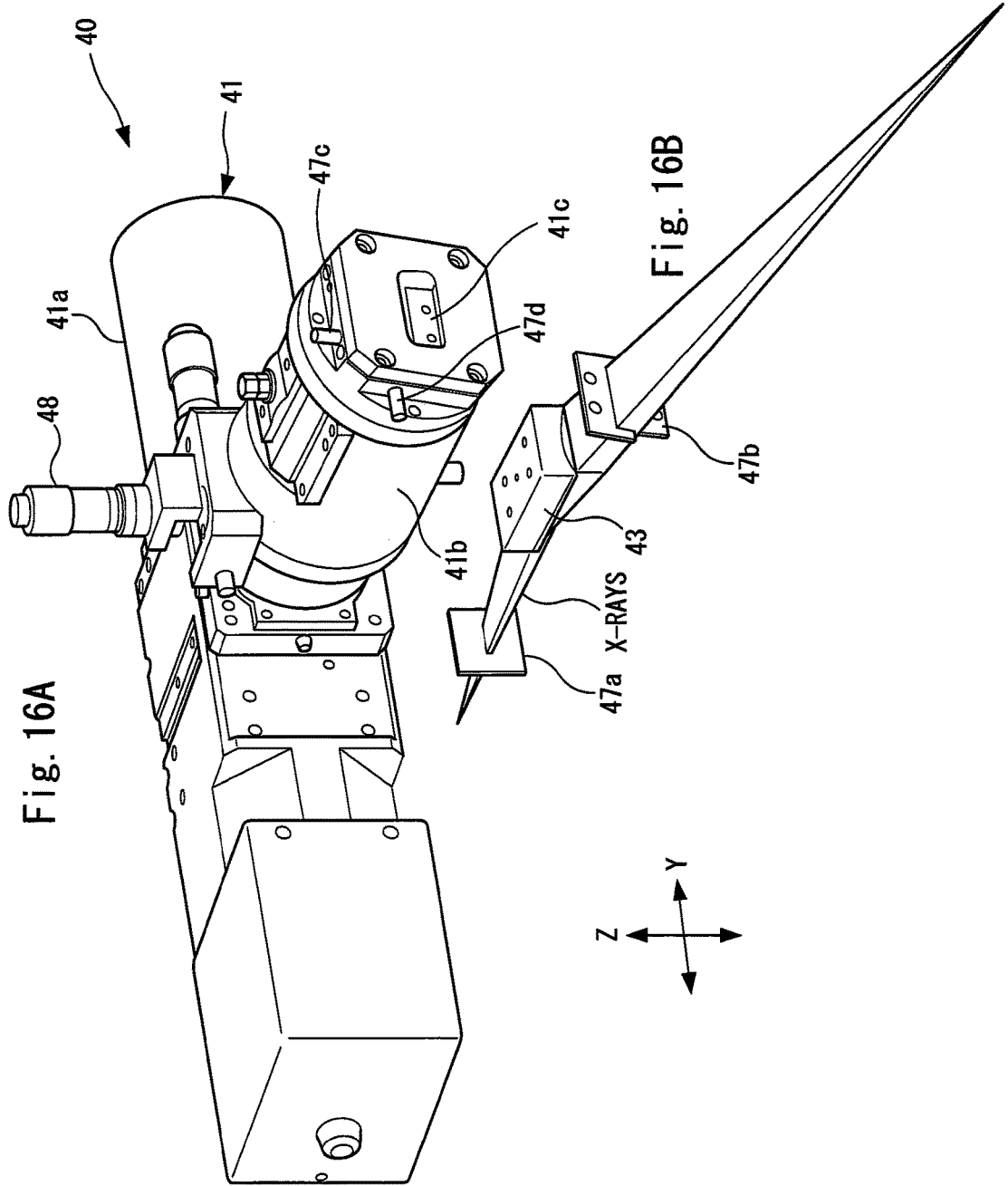
FIG. 16 is a perspective view showing the appearance of a second embodiment according to the X-ray irradiation unit.

The X-ray irradiation unit 40 has an exterior appearance as shown in FIG. 16, and designed in a module configuration that an X-ray tube 42 as an X-ray source and an X-ray optical element 43 are incorporated in a tube shield (unit main body) 41. The tube shield 41 is formed of a metal material for shielding X-rays, and divided into a first tube 41a containing the X-ray tube 42, and a second tube 41b containing the X-ray optical element 43. The respective tubes 41a and 41b are joined to each other through a joint member 41d.

Figure 17:
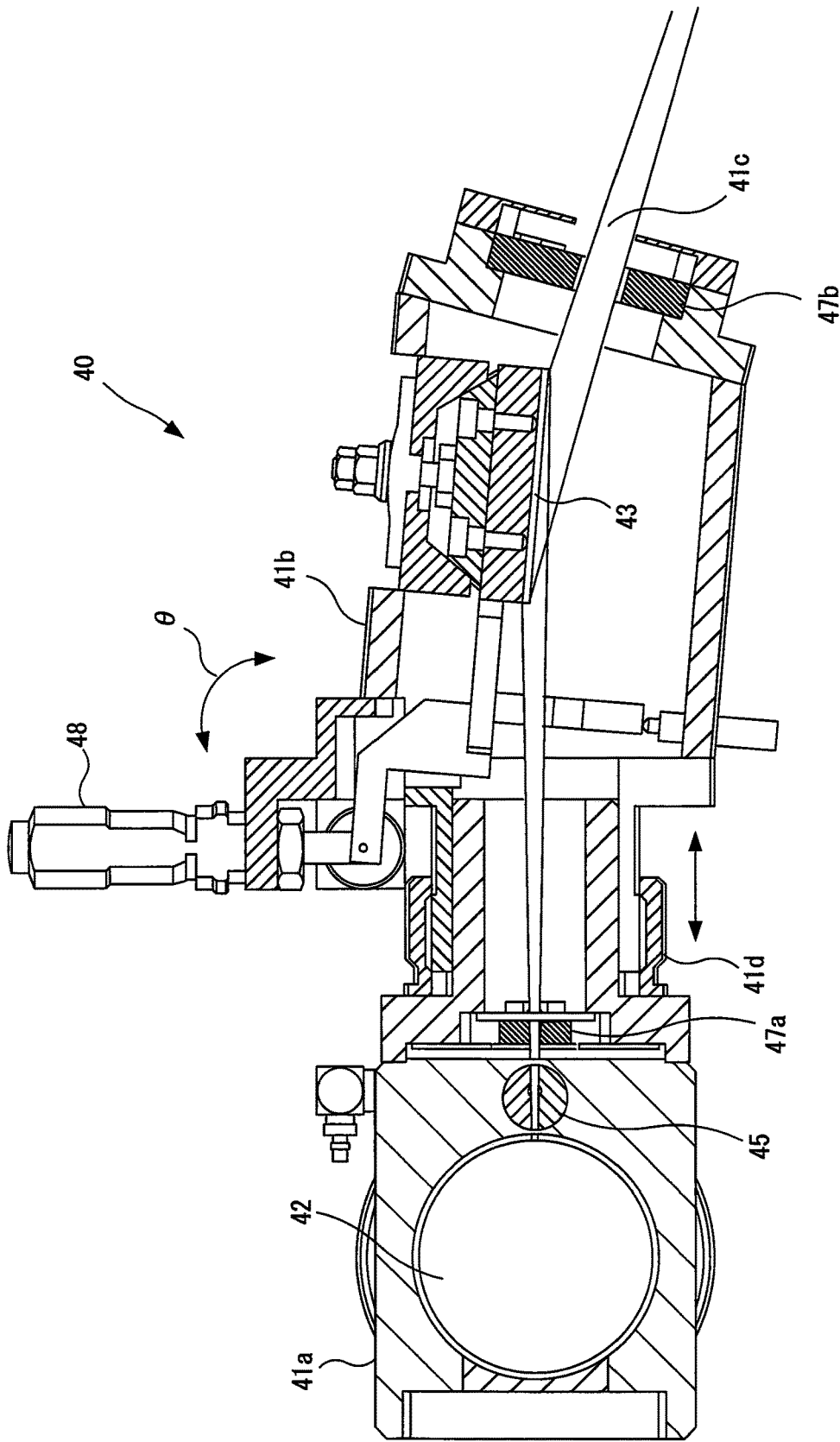
FIG. 17 is a longitudinally-sectional view showing the configuration of the second embodiment according to the X-ray irradiation unit.

As shown in FIGS. 16B and 17, an X-ray path for leading X-rays radiated from the X-ray tube 42 to an X-ray emission port 41c is formed in the tube shield 41, and a shutter 45 for opening/closing the X-ray path is arranged in the first tube 41a. The shutter 45 is configured to open/close by its rotation, thereby passing or shielding X-rays radiated from the X-ray tube 42.

Gold (Au), molybdenum (Mo) or the like may be selected as the target material of the X-ray tube 42 as required. Other materials such as copper (Cu), iron (Fe), cobalt (Co), tungsten (W), chromium (Cr), silver (Ag), etc. may be used.

Figure 18:
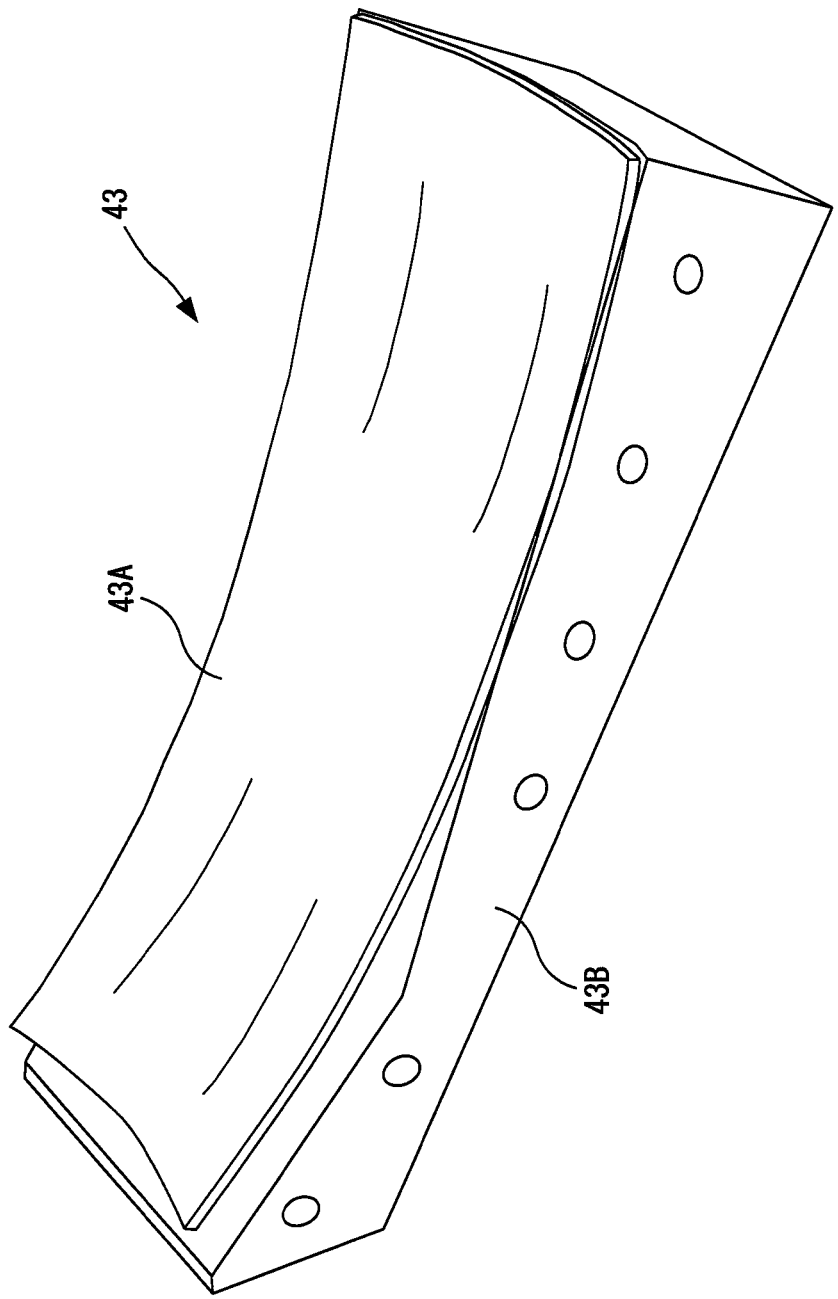
FIG. 18 is a perspective view showing the appearance of an X-ray optical element in the X-ray irradiation unit shown in FIG. 17.

As shown in FIG. 18, the X-ray optical element 43 is configured by fixing a double curved monochromator crystal plate (DCC) 43A to a support block 43B. The double curved monochromator crystal plate (DCC) 43A comprises a semiconductor single crystal plate which has a reflection surface having a high-order curved surface of a tertiary or higher order curved surface and is formed of germanium (Ge), silicon (Si), gallium arsenide (GaAs) or the like. The X-ray optical element 43 is configured to be curved not only in the length direction for setting of the acceptance angle for X-rays, but also in the width direction perpendicular to the length direction for setting of the acceptance angle for X-rays, whereby X-rays from the X-ray tube 42 are reflected with a large area at a large acceptance angle to enable irradiation of X-rays having large intensities. The X-ray optical element 43 has a function of monochromatizing X-rays incident thereto. For example, in the case of the X-ray tube 42 using an Mo target, X-rays are monochromatized to Mo—K$\alpha$, and in the case of the X-ray tube 42 using an Au target, X-rays are monochromatized to Au-L$\beta$.

The aforementioned double curved monochromator crystal plate 43A having the reflection surface with the high-order curved surface of a tertiary or higher order curved surface can be manufactured by a high-temperature embossing method disclosed in International Publication No. WO2007/072906, for example. For example, a flat-plate-shaped semiconductor single crystal plate is inserted in an embossing member and subjected to plastic deformation under a high temperature and high pressure condition, thereby manufacturing the double curved monochromator crystal plate 43A configured to have a large area and a large acceptance angle and also have a high-order curved surface of a tertiary or higher order curved surface. Here, the crystal lattice plane of the double curved monochromator crystal plate 43A is adjusted to satisfy an asymmetrical Johann type or Logarithmic spiral type X-ray diffraction condition, for example.

Returning to FIGS. 16 and 17, the X-ray irradiation unit 40 has an incident aperture 47a and an exit aperture 47b arranged in the tube shield 41. The incident aperture 47a serves as a transmission window member for throttling X-rays radiated from the X-ray tube 42 and efficiently irradiating the X-rays to the reflection surface of the double curved monochromator crystal plate 43A. The exit aperture 47b serves as a transmission window member for throttling X-rays reflected from the double curved monochromator crystal plate 43A, and efficiently focusing and leading the X-rays to the focal point.

The incident aperture 47a is provided with an opening portion for transmitting X-rays therethrough at the center portion of a shielding member formed of a metal material capable of shielding X-rays. The exit aperture 47b is provided with an opening portion for transmitting X-rays therethrough at the center portion of a shielding member formed of a metal material capable of shielding X-rays, and is configured to make the shielding member movable in a height direction (Z-direction) and a width direction (Y-direction) which are perpendicular to each other. The height position of the opening portion for transmitting X-rays therethrough is minutely adjustable by a height adjusting screw 47c provided to the second tube 41b, and also the position in the width direction of the opening portion for transmitting X-rays therethrough is minutely adjustable by a lateral position adjusting screw 47d provided to the second tube 41b.

As shown in FIG. 17, the joint member 41d of the tube shield 41 is configured to be adjustable in movement in the optical path direction of X-rays radiated from the second tube 41b relatively to the first tube 41a, whereby the position of the reflection surface of the X-ray optical element 43 can be minutely adjusted with respect to the optical path of X-rays radiated from the X-ray tube 42. Furthermore, the first tube 41a is configured to be swingable in the direction of an arrow $\theta$ of FIG. 17 relatively to the joint member 41d, and the swing angle $\theta$ can be minutely adjusted by operating a micrometer 48, whereby the incident angle $\theta$ of X-rays radiated from the X-ray tube 42 to the reflection surface of the X-ray optical element 43 can be minutely adjusted.

Figure 19:
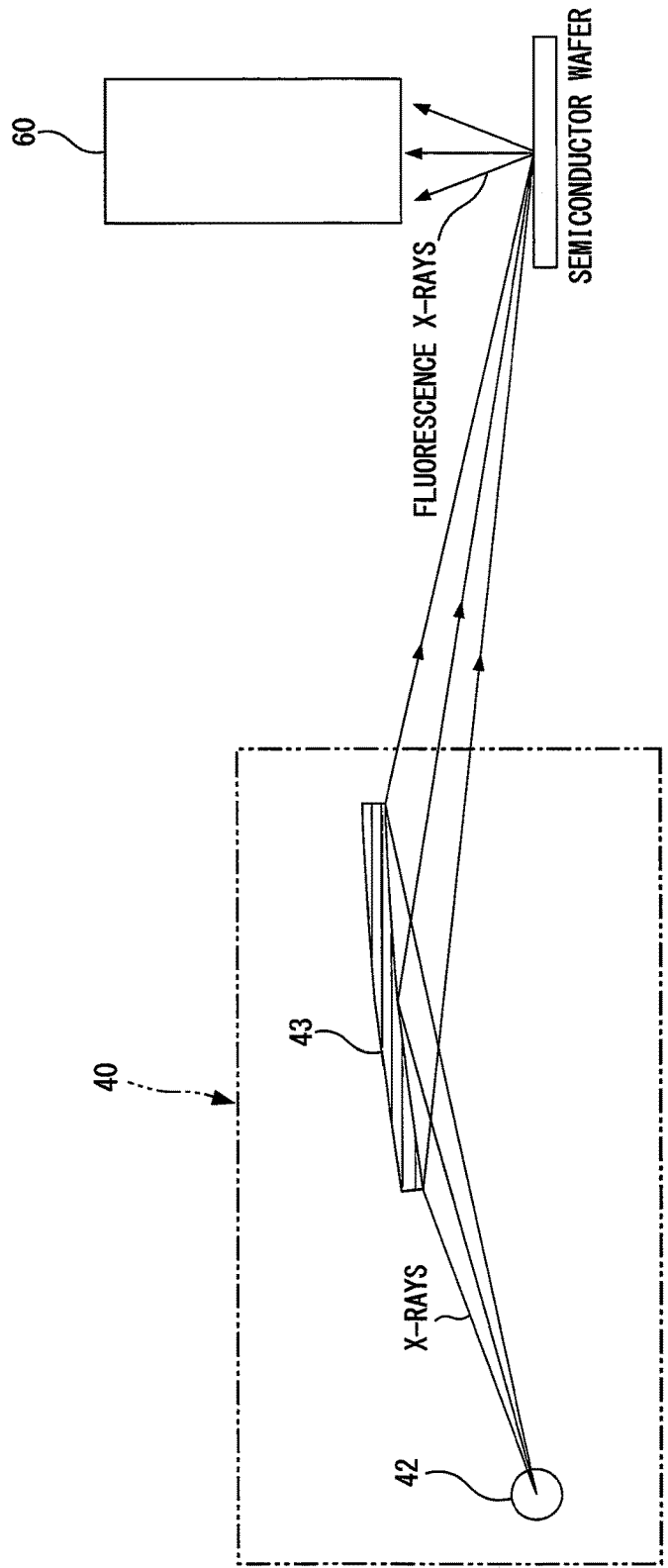
FIG. 19 is a schematic diagram showing a fluorescence X-rays measurement using the X-ray irradiation unit shown in FIG. 17.

The X-ray irradiation unit 40 having the aforementioned configuration can form an optical system suitable for the fluorescence X-ray measurement as shown in FIG. 19. That is, X-rays radiated from the X-ray tube 42 are monochromatized, reflected and focused by the X-ray optical element 43, and then irradiated to the inspection target face of the semiconductor wafer. Then, fluorescence X-rays appearing from the semiconductor wafer are captured by the fluorescence X-ray detector 60, and analyzed.

Each of the X-ray irradiation unit 40 according to the first embodiment shown in FIGS. 6 to 15 and the X-ray irradiation unit 40 according to the second embodiment shown in FIGS. 16 to 19 can be installed on the first rotation arm 32 of the X-ray thin film inspection device shown in FIG. 1. For example, the X-ray irradiation unit 40 arranged at the center position out of the three installed X-ray irradiation units 40 is set as the X-ray irradiation unit 40 according to the first embodiment shown in FIGS. 6 to 15, the X-ray irradiation unit 40 arranged at the upper side is set as the X-ray irradiation unit 40 for radiating X-rays of Au-L$\beta$ according to the second embodiment shown in FIGS. 16 to 19, and further the X-ray irradiation unit 40 at the lower side is set as the X-ray irradiation unit 40 for radiating X-rays of Mo—Kα according to the second embodiment shown in FIGS. 16 to 19.

When the various kinds of X-ray irradiation units 40 are installed on the first rotation arm 32 as described above, the X-ray irradiation units 40 which are suitable for the X-ray reflectivity measurement and the fluorescence X-ray measurement can be efficiently set up in a short time by merely rotating the X-ray irradiation units 40.

[Temperature Correction System]

Next, a temperature correction system for the X-ray thin film inspection device will be described in detail.

When the internal temperature of the X-ray thin film inspection device varies, the respective members constituting the device expands or contract although it is slight, and the inspection position of the device which is the irradiation point of X-rays varies three-dimensionally. For example, a minute pattern (a site-under-measurement) of a semiconductor wafer is disposed at an inspection position, and X-rays are irradiated to this inspection position. However, when the inspection position varies due to temperature variation, the minute pattern of the semiconductor wafer as a site-under-measurement cannot be properly irradiated with X-rays, which may cause decrease of the precision of measurements based on X-rays.

A high-precision temperature management is performed on the inside of a clean room in which a semiconductor manufacturing line is established, and for example, the temperature variation is kept within 1° C. However, the minute pattern of the semiconductor wafer as the site-under-measurement has a minute area of several tens μm. In a process of irradiating this minute area with focused X-rays to perform an X-ray inspection, even a positional variation of micron order greatly affects the measurement result.

Therefore, the X-ray thin film inspection device according to this embodiment is incorporated with a temperature correction system for correcting variation of an inspection position (irradiation position of X-rays) due to temperature variation and matching the inspection position with the irradiation point of the X-rays.

<Principle of Temperature Correction>

The temperature correction system of the X-ray thin film inspection device according to this embodiment corrects the positional variation following temperature variation on the basis of the following principle.

When factors causing variation of the inspection position (X-ray irradiation position) following temperature variation (positional variation factors) are roughly classified, movement of an X-ray beam, movement of an inspection target and movement of the optical microscope 70 are considered. For example, the X-ray beam moves due to expansion/contraction of the goniometer 30 or the like, the inspection target moves due to expansion/contraction of the sample stage 10 or the like, and an observation position of the optical microscope 70 moves due to expansion/contraction of a support frame for supporting the optical microscope 70 or the like.

Therefore, with respect to the positional variation factors of n following temperature variation, the positional variation following temperature variation of each positional variation factor is estimated in consideration of an coefficient relating to time-lapse (time constant τ) and a coefficient relating to temperature variation (temperature constant C) of the positional variation factor.

Specifically, the time constant and temperature constant of an n-th positional variation factor are represented by τn and Cn, respectively. The temperature is successively measured at a time interval of t seconds, and it is assumed that the measured temperature under an i-th measurement (measurement time t[i]) from the start of the measurement is equal to $T_M[i]$. At this time, the effective temperature $T_E n[i]$ can be calculated by the following recurrence formula(1).

[Formula 1]

$$T_E n[i] = \frac{T_M[i] \times (t[i] - t[i-1]) + T_E n[i-1] \times \tau_n}{t[i] - t[i-1] + \tau_n} \quad (1)$$

When the difference between the measured temperature $T_M[0]$ at the start time of the temperature measurement and the effective temperature $T_E n[0]$ is represented by ΔTn, the relationship of the following formula (2) is satisfied therebetween.

[Formula 2]

$$T_E n[0] = T_M[0] + \Delta T n \quad (2)$$

The temperature constant Cn corresponds to the positional variation amount for variation of the effective temperature by 1° C. The positional variation ΔZ[i] in the height direction (Z-direction) at the i-th measurement time point (measurement time t[i]) from the start of the measurement can be estimated according to the following formula (3) by using the effective temperature $T_E n[i]$ and the temperature constant Cn of each positional variation factor.

[Formula 3]

$$\Delta Z[i] = \sum_{K=1}^{i} \sum_{n=0}^{N-1} C_n (T_E n[K] - T_E n[K-1]) \quad (3)$$

Accordingly, the inspection position Z[i] in the height direction at the i-th measurement time point (measurement time t[i]) from the start of the measurement can be estimated according to the following formula (4) by adding the positional variation ΔZ[i] following temperature variation to a reference position Z[0] which is a position under the state that there is not any positional variation following temperature variation.

[Formula 4]

$$Z[i] = Z[0] + \sum_{K=1}^{i} \sum_{n=0}^{N-1} C_n (T_E n[K] - T_E n[K-1]) \quad (4)$$

The reference position Z[0] corresponds to the inspection position at the start time of the temperature measurement. However, it is realistically difficult to estimate the difference $\Delta T_n$ between the measured temperature and the effective temperature with respect to each positional variation factor at the start time of the temperature measurement. Therefore, it is preferable to set ΔTn to zero and use temperature measurement data after sufficient time elapses as compared with the time constant of each positional variation factor. This is likewise applied to a case where the positional variations in the width direction (Y-direction) and the optical path direction (X-direction) are determined as described later.

The time constant τn and the temperature constant Cn of each positional variation factor can be determined by actually measuring the inspection position in the height direction (Z-direction) at each of measurement time points (measurement times t[i]) from the start of the measurement till the i-th measurement, substituting the measured inspection position into Z[i] in the above formula (4) and applying the least-squares method.

When the variables (the time constant Tn and the temperature constant Cn) of each positional variation factor are determined as described above, these variables are substituted into the above formulas (1) and (3), and the positional variation ΔZ[i] in the height direction at the inspection position at the measurement time t[i] can be calculated from the data of the measured temperature $T_M[i]$ based on the respective formulas.

Next, the positional variation ΔX[i] in the length direction (X-direction) on the horizontal plane at the measurement time point (the measurement time t[i]) of the i-th measurement from the start of the measurement can be estimated by using the effective temperature $T_En[i]$ and the temperature constant Cn of each positional variation factor according to the formula (5).

[Formula 5]

$$\Delta X[i] = \sum_{K=1}^{i} \sum_{n=0}^{N-1} C_n(T_E n[K] - T_E n[K-1]) \quad (5)$$

Accordingly, the inspection position X[i] in the length direction (X-direction) on the horizontal plane at the measurement time point (measurement time t[i]) of the i-th measurement from the start of the measurement can be estimated according to the following formula (6) by setting a reference position X[0] under the state that there is no positional variation following temperature variation, and adding the reference position X[0] with the positional variation ΔX[i] following temperature variation described above.

[Formula 6]

$$X[i] = X[0] + \sum_{K=1}^{i} \sum_{n=0}^{N-1} C_n(T_E n[K] - T_E n[K-1]) \quad (6)$$

The time constant τn and the temperature constant Cn of each positional variation factor can be determined by actually measuring the inspection position in the length direction (X-direction) on the horizontal plane at the measurement time point (measurement time t[i]) of the i-th measurement from the start of the measurement, substituting the measured inspection position into X[i] in the above formula (6) and applying the least-squares method.

When the variables (the time constant τn and the temperature constant Cn) of each positional variation factor are determined as described above, these variables are substituted into the formula (1) and the formula (5), and the positional variation ΔX[i] in the length direction (X-direction) on the horizontal plane at the inspection position at the measurement time t[i] can be calculated from the data of the measured temperature $T_M[i]$ on the basis of the respective formulas.

Furthermore, the positional variation ΔY[i] in the width direction (Y-direction) on the horizontal plane at the measurement time point (measurement time t[i]) of the i-th measurement from the start of the measurement can be estimated according to the following formula (7) by using the effective temperature $T_En[i]$ and the temperature constant Cn of each positional variation factor.

[Formula 7]

$$\Delta Y[i] = \sum_{K=1}^{i} \sum_{n=0}^{N-1} C_n(T_E n[K] - T_E n[K-1]) \quad (7)$$

Accordingly, the inspection position Y[i] in the width direction (Y-direction) on the horizontal plane at the measurement time point (measurement time t[i]) of the i-th measurement from the start of the measurement can be estimated according to the following formula (8) by setting a reference position Y[0] under the state that there is no positional variation following temperature variation, and adding the reference position Y[0] with the positional variation ΔY[i] following temperature variation described above.

[Formula 8]

$$Y[i] = Y[0] + \sum_{K=1}^{i} \sum_{n=0}^{N-1} C_n(T_E n[K] - T_E n[K-1]) \quad (8)$$

The time constant τn and the temperature constant Cn of each positional variation factor can be calculated by actually measuring the inspection position in the width direction (Y-direction) on the horizontal plane at the measurement time point (measurement time t[i]) of the i-th measurement from the start of the measurement, substituting the measured inspection position into Y[i] in the above formula (8) and applying the least-squares method.

When the variables (the time constant τn and the temperature constant Cn) of each positional variation factor are determined as described above, these variables are substituted into the formula (1) and the formula (7), and the positional variation ΔY[i] in the width direction (Y-direction) on the horizontal plane at the inspection position at the measurement time t[i] can be calculated from the data of the measured temperature $T_M[i]$ on the basis of the respective formulas.

<Summary of Temperature Correction System>

The temperature correction system according to this embodiment is configured to execute the temperature correction method described later based on temperature correction software stored in the central processing unit 100 shown in FIG. 3.

Furthermore, the X-ray thin film inspection device has a temperature measuring unit 110 as a constituent element of the temperature correction system (see FIG. 3). Various well-known temperature sensors or a thermocouple may be used as the temperature measuring unit 110. Originally, the internal temperature of each of various kinds of constituent elements of the device, which is a positional variation factor following temperature variation, should be measured by the temperature measuring unit. However, it is difficult and unrealistic to measure the internal temperatures of many constituent members one by one. Therefore, according to this embodiment, the time constant Tn and the temperature constant Cn are determined so as to make it unnecessary to measure the internal temperatures of various kinds of constituent elements of the device one by one. Therefore, the temperature may be measured at a point which is representative of the external temperatures of all the members constituting the device. Specifically, the temperature of air in an inspection chamber where the X-ray thin film inspection device is installed or the temperature of air exhausted from an exhaust port of the inspection chamber is measured, and the measured temperature is set as the measured temperature $T_M[i]$ in the aforementioned formula (1).

<Temperature Correction Method>

The central processing unit 100 executes the following temperature correction method based on the stored temperature correction software. The temperature correction method is divided into a preparation stage for determining the time constant τn and the temperature constant Cn of the positional variation factor in the above principle, and an execution stage for repeating the temperature measurement and the position correction based on the formulas (1), (3), (5) and (7) in which the determined time constant τn and temperature constant Cn of the positional variation factor are substituted.

First, the preparation stage for determining the time constant τn and the temperature constant Cn of the positional variation factor will be described.

Figure 20:
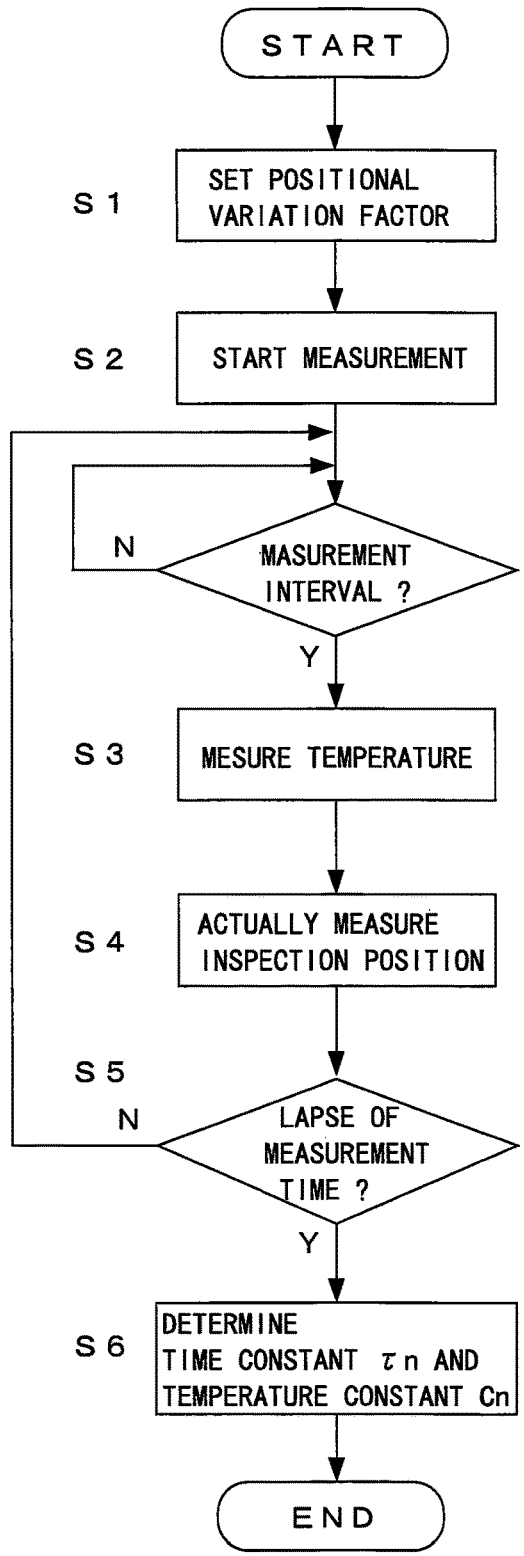
FIG. 20 is a flowchart showing steps for a preparation stage in an embodiment according to a temperature correction system.

As shown in the flowchart of FIG. 20, in the preparation stage, a positional variation factor following temperature variation is set, and the measurement thereof is started (steps S1, S2). The temperature measurement and the actual measurement of the inspection position are performed at a fixed measurement interval (steps S3, S4). The temperature measurement and the actual measurement of the inspection position are repetitively executed for only a predetermined time (step S5).

When there is any positional variation in the height direction (Z-direction), the acquired measurement data are substituted into $Z[i]$ in the above formula (4), and the time constant τn and the temperature constant Cn of the positional variation factor are calculated by the least-squares method (step S6). Likewise, when there is any positional variation in the length direction (X-direction) on the horizontal plane, the acquired measurement data are substituted into $X[i]$ in the above formula (6), and the time constant τn and the temperature constant Cn of the positional variation factor are calculated by the least-squares method (step S6). When there is any positional variation in the width direction (Y-direction) on the horizontal plane, the acquired measurement data are substituted into $Y[i]$ in the above formula (8), and the time constant τn and the temperature constant Cn of the positional variation factor are calculated by the least-squares method (step S6).

Here, the actual measurement of the inspection position in the height direction (the Z-direction) can be performed according to the following procedure.

Figure 21:
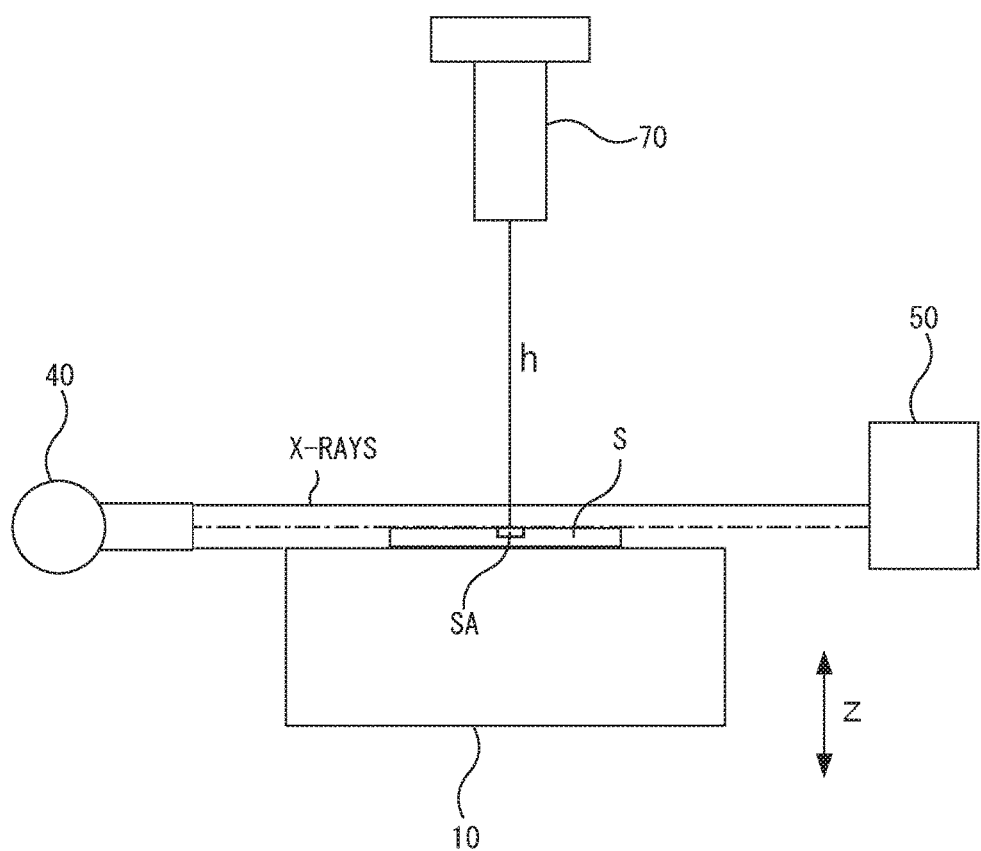
FIG. 21 is a schematic diagram showing the actual measurement procedure of an inspection position in a Z-direction in the embodiment according to the temperature correction system.

First, as shown in FIG. 21, a sample S for temperature correction is disposed on the upper surface of the sample stage 10, and a site-under-measurement SA of the sample S is moved to a position below the optical microscope 70. Subsequently, the respective rotation arms 32 and 33 of the goniometer 30 are rotated and set so that a predetermined X-ray irradiation unit 40 and the X-ray detector 50 are arranged at both the sides of the sample stage 10 so as to horizontally face each other through the sample stage 10. In such an arrangement relationship, the center axis of X-rays radiated from the X-ray irradiation unit 40 is horizontal, and thus the X-rays are incident to the center of the detection face of the X-ray detector 50 which is arranged to face the X-ray irradiation unit 40.

Subsequently, the sample stage 10 located at the intermediate position is moved and adjusted in the height direction (Z-direction) so that the X-ray intensity detected by the X-ray detector 50 is half the intensity of X-rays radiated from the X-ray tube 42. Accordingly, the sample S is disposed at a position where the half of the X-rays radiated from the X-ray tube 42 is shielded by the sample stage 10 and the side surface of the sample S, and the residual half of the X-rays passes above the sample S and then are incident to the X-ray detector 50. With this arrangement, the upper surface of the sample S is coincident with the center axis of the X-rays radiated from the X-ray tube 42. The height position serves as the inspection position in the height direction. Therefore, when an X-ray thin film inspection is performed, X-rays from the X-ray irradiation unit 40 are irradiated to this height position. The series of these operations is generally referred to "sample surface centering".

Next, the focal point of the optical microscope 70 is matched with the site-under-measurement SA of the sample S by using an auto focusing mechanism of the optical microscope 70 as shown in FIG. 21, and the distance h from the optical microscope 70 to the upper surface of the sample S is measured. In this embodiment, this distance h is set as the actual measured position in the height direction (Z-direction) associated with the inspection position.

Next, the actual measurement procedure of the inspection position in the length direction (X-direction) and the width direction (Y-direction) which are perpendicular to each other on the horizontal plane will be described.

Figure 22A:
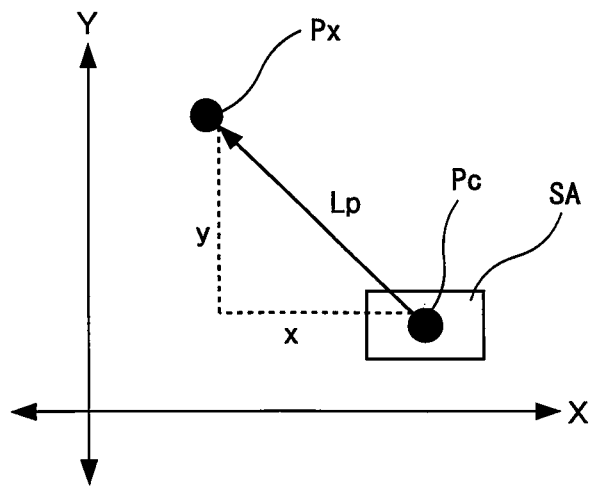
FIG. 22 is a schematic diagram showing the actual measurement procedure of inspection positions in X-direction and Y-direction in the embodiment according to the temperature correction system.
Figure 22B:
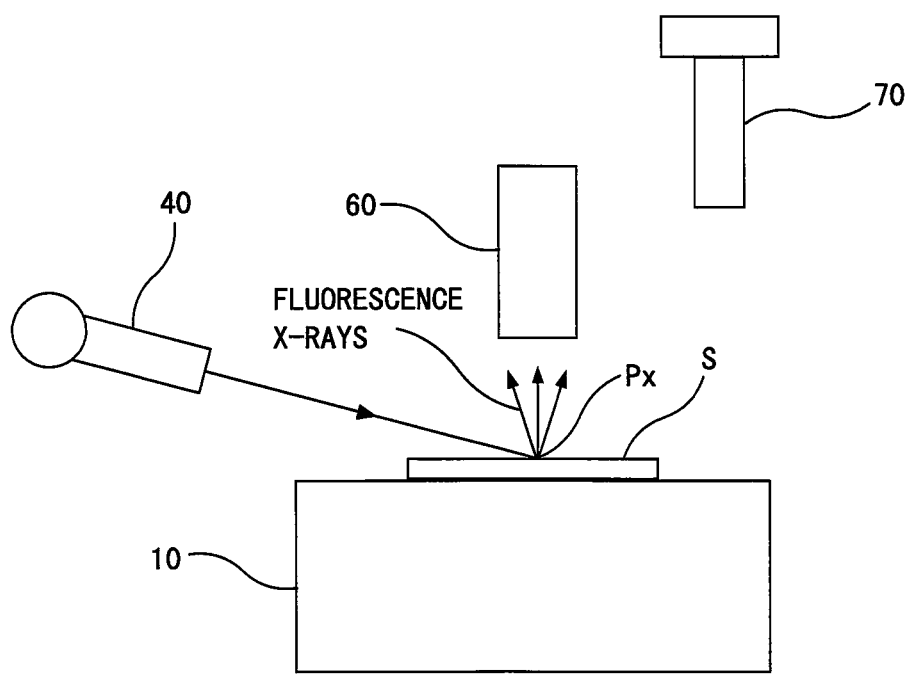

In the X-ray thin film inspection device shown in FIG. 1, an inspection position (the irradiation position of X-rays by the X-ray irradiation unit 40) Px and an observation position Pc by the optical microscope 70 are set to be spaced from each other on the horizontal plane by only a distance Lp as shown in FIG. 22A. This is because the fluorescence X-ray detector 60 is installed above the inspection position and thus the optical microscope 70 cannot be installed at the same position as shown in FIG. 22B.

Therefore, as shown in FIG. 22A, the sample stage 10 is first horizontally moved so that the measurement point SA of the sample S disposed on the upper surface of the sample stage 10 is located at the center of the observation position Pc of the optical microscope 70. This can be performed as follows. A picture captured by the optical microscope 70 is subjected to pattern recognition by the pattern recognition circuit 102, and the central processing unit 100 controls the positioning mechanism 20 based on the image.

Subsequently, the measurement point SA of the sample S disposed at the inspection position is moved to and located at the inspection position Px. This can be performed by horizontally moving the sample stage 10 while X-rays are radiated from the X-ray irradiation unit 40 to the inspection position Px, and detecting fluorescence X-rays emitted from the sample S by the fluorescence X-ray detector 60 as shown in FIG. 22B. That is, when the measurement point SA of the sample S is located at the inspection position Px (that is, the irradiation position of X-rays by the X-ray irradiation unit 40), the intensity of the fluorescence X-rays detected by the fluorescence X-ray detector 60 reaches a peak intensity. The sample S for temperature correction is formed of a material which excites fluorescence X-rays upon radiation of X-rays thereto.

In this embodiment, the movement amount x in the length direction (X-direction) when the measurement point SA of the sample S disposed on the sample stage 10 is moved from the observation position of the optical microscope 70 to the inspection position Px is set as the actual measured position in the length direction (X-direction) on the horizontal plane with respect to the inspection position of the sample stage 10.

Likewise, the movement amount y in the width direction (Y-direction) when the measurement point SA of the sample S disposed at the inspection position of the sample stage 10 is moved from the observation position of the optical microscope 70 to the inspection position Px is set as the actual measured position in the width direction (Y-direction) on the horizontal plane with respect to the inspection position of the sample stage 10.

In the execution stage of the temperature correction, the time constant τn and the temperature constant Cn of the position variation factor which are determined according to the aforementioned procedure are set as parameters of the above formulas (1), (3), (5) and (7), and the central processing unit 100 executes the temperature correction based on these formulas. This execution stage of the temperature correction is executed in parallel to execution of the thin film inspection of X-rays. That is, during the execution of the thin film inspection of X-rays, the central processing unit 100 receives temperature measurement data transmitted from the temperature measuring unit 110, calculates the positional variation following temperature variation at the inspection position according to the formulas (1), (3), (5) and (7) based on the temperature measurement data, and minutely adjusts the position of the sample stage by only the variation amount.

Accordingly, the inspection position of the sample stage 10 is matched with the irradiation point of X-rays at all times, and high-precision X-ray thin film inspection can be performed.

Furthermore, the inventors of the present application focused on the difference in time constant among the respective members constituting the X-ray thin film inspection device as a factor of the positional variation following temperature variation, sorted these members into members having large time constants τ and members having small time constants τ (that is, N=2), and could correct the positional variation following temperature variation with remarkably high precision when the above two positional variation factors were set and the aforementioned temperature correction was executed. The time constant is determined by the specific heat and coefficient of thermal expansion of each member and the heat conduction distance. For example, a thin pipe member has a small time constant, and a large-size member has a large time constant.

Figure 23:
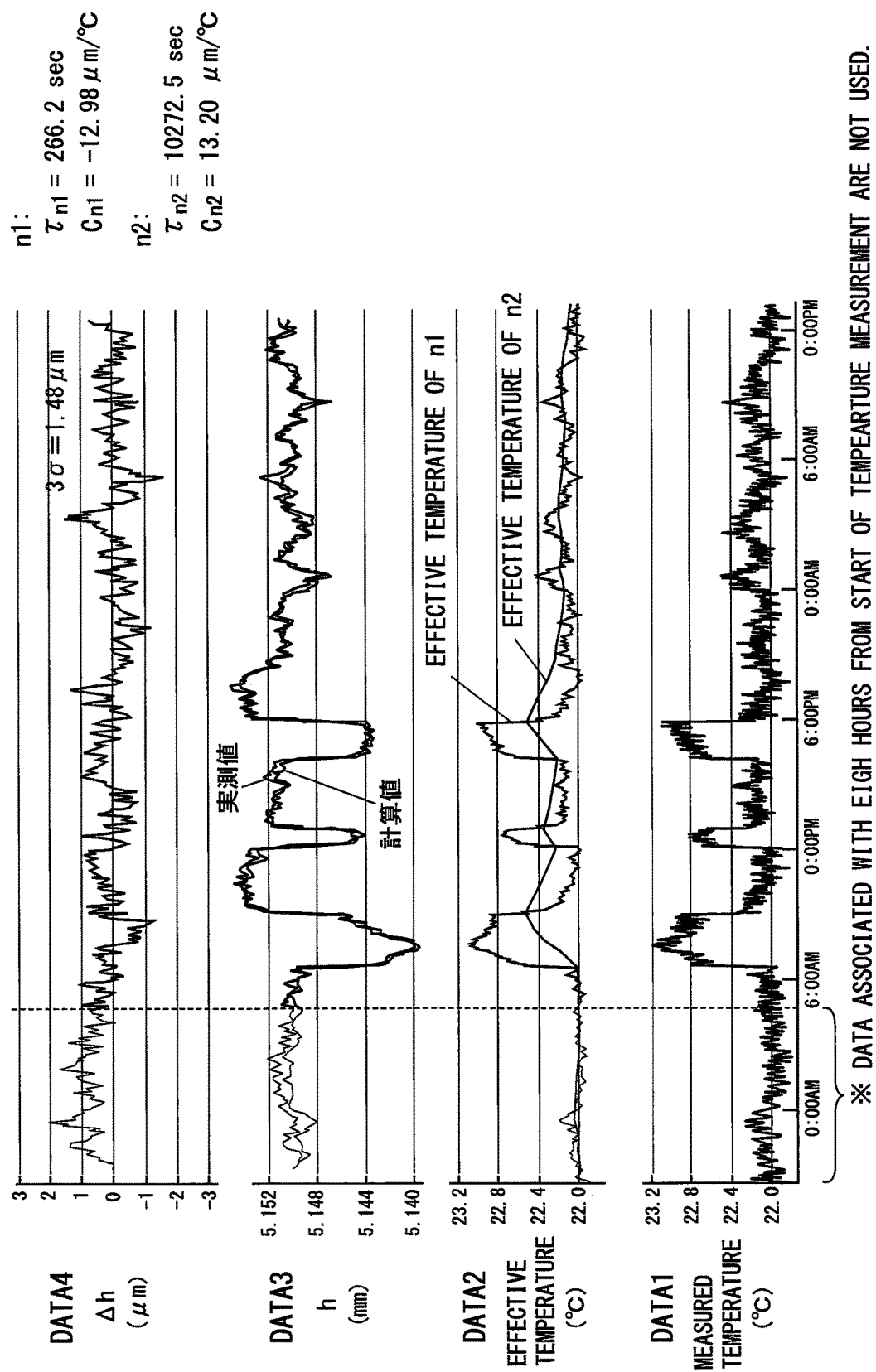
FIG. 23 is a graph showing an experiment result related to temperature correction obtained by inventors.

FIG. 23 is a graph showing experimental results achieved by the inventors.

By targeting an X-ray thin film inspection device installed in a clean room where a semiconductor manufacturing line is established, the internal temperature of the device was measured, and the positional variation following temperature variation of the device was corrected.

Two positional variation factors following temperature variation, one of which was a small time constant of 266.2 seconds (positional variation factor n1) and the other of which was a large time constant of 10272.5 seconds (positional variation factor n2), were set in this experiment, and the calculation value of the distance h from the optical microscope 70 to the upper surface of the sample stage 10 was determined based on the above formula (4) (see DATA3 of FIG. 23). The temperature constant of the positional variation factor n1 was equal to −12.98 μm/° C., and the temperature constant of the positional variation factor n2 was equal to 13.20 μm/° C.

As a calculation result of the difference (that is, variation amount) between the calculation value and the measured value for the distance h from the optical microscope 70 to the upper surface of the sample stage 10, the variation amount shows a remarkably small value as shown in DATA4 of FIG. 23, and thus it was verified that the positional variation following temperature variation could be corrected with high precision by the temperature correction system of the present invention.

[Improvement of X-Ray Reflectivity Measurement System]

Next, an improvement of a system for the X-ray reflectivity measurement of the X-ray thin film inspection device will be described.

As well known, the X-ray reflectivity measurement is suitable for measuring, particularly the thickness of a thin film, the roughness of the surface of a thin film, the roughness of the interface between a thin film and a base material, the density of a thin film, etc. The principle of this X-ray reflectivity measurement is as follows (see FIGS. 24 and 25).

Figure 24A:
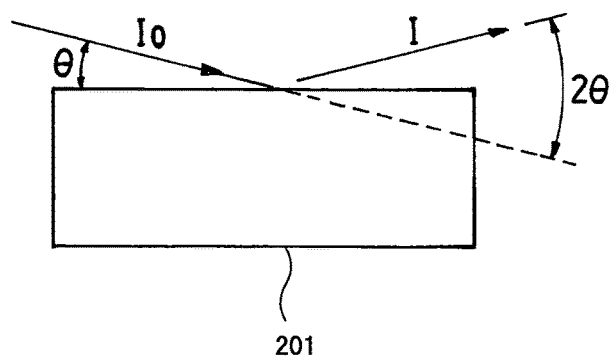
FIGS. 24A and 24B are diagrams showing the principle of X-ray reflectivity measurement.
Figure 24B:
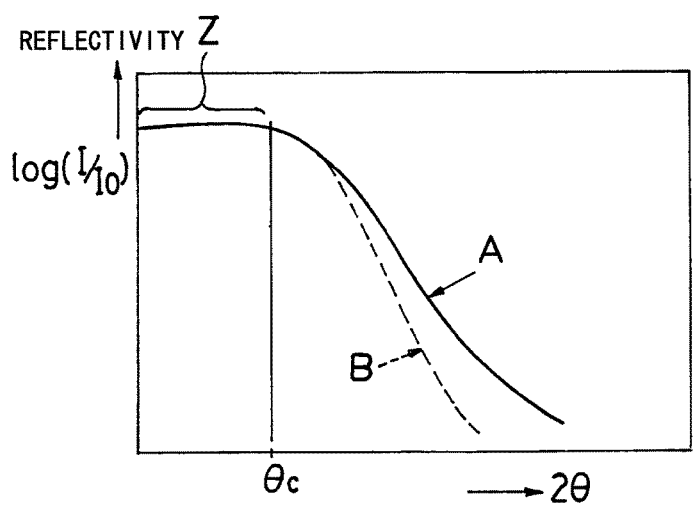

When X-rays is incident very closely to the surface of a material 201 having a flat surface, that is, X-rays is incident from a low angle θ in FIG. 24A, total reflection occurs at a critical angle or less. The critical angle is very small. For example, in the case of X-rays of CuKα, the critical angle is equal to 0.22° for Si or glass plate, 0.42° for Ni, and 0.57° for Au.

This critical angle varies depending on the electron density of the material. As the incident angle of X-rays becomes larger than the critical angle, the X-rays gradually infiltrates more deeply into the material. In the case of a material having an ideal flat surface, the X-ray reflectivity decreases sharply in proportion to $\theta^{-4}$ (θ represents X-ray incident angle) at the critical angle θc or more as indicated by a curved line A in FIG. 24B. Furthermore, when the surface of the material is rough, the decreasing degree is further greater as indicated by a broken line B. On the ordinate axis of FIG. 24B, $I_0$ represents the incident X-ray intensity, and I represents the reflected X-ray intensity.

Figure 25A:
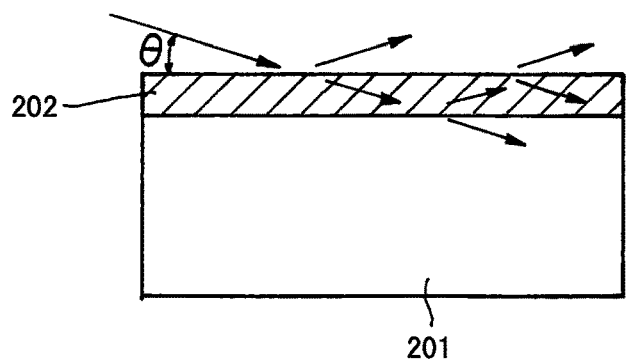
FIGS. 25A and 25B are diagrams showing the principle of the X-ray reflectivity measurement.
Figure 25B:
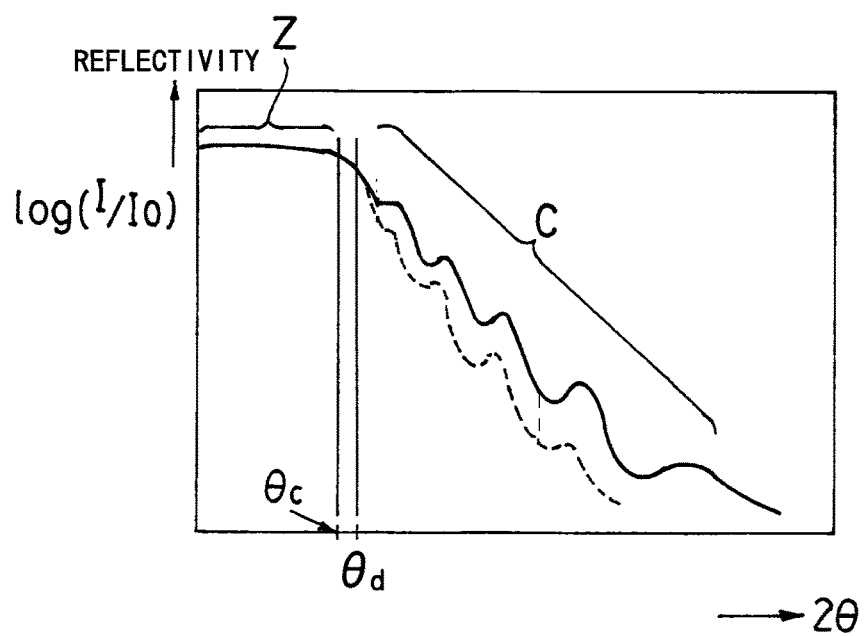

As shown in FIG. 25A, the aforementioned material is used as a substrate 201, and another material having a different electron density is uniformly laminated on the substrate 201 to form a thin film 202. When X-rays are incident at a low angle, X-rays reflected from the boundary between the substrate 201 and the thin film 202 and X-rays reflected from the surface of the thin film 202 mutually intensify or weaken each other. As a result, an oscillation pattern C caused by the interference of the X-rays appears in a reflectivity curved line as shown in FIG. 25B.

The thickness of the thin film 202 can be determined from the period of the oscillation pattern C, and information on the surface and the interface can be obtained from the angle-dependence of the amplitude of the oscillation pattern C. Furthermore, by considering both the period and amplitude of the oscillation pattern in combination, the density of the thin film 202 is determined.

When the X-ray reflectivity measurement (XRR) is performed by the X-ray thin film inspection device, a one-dimensional X-ray detector may be used in place of the avalanche photodiode (APD) described above to acquire X-ray detection data according to a scanning system called as "TDI (Time Delay Integration).

Figure 26:
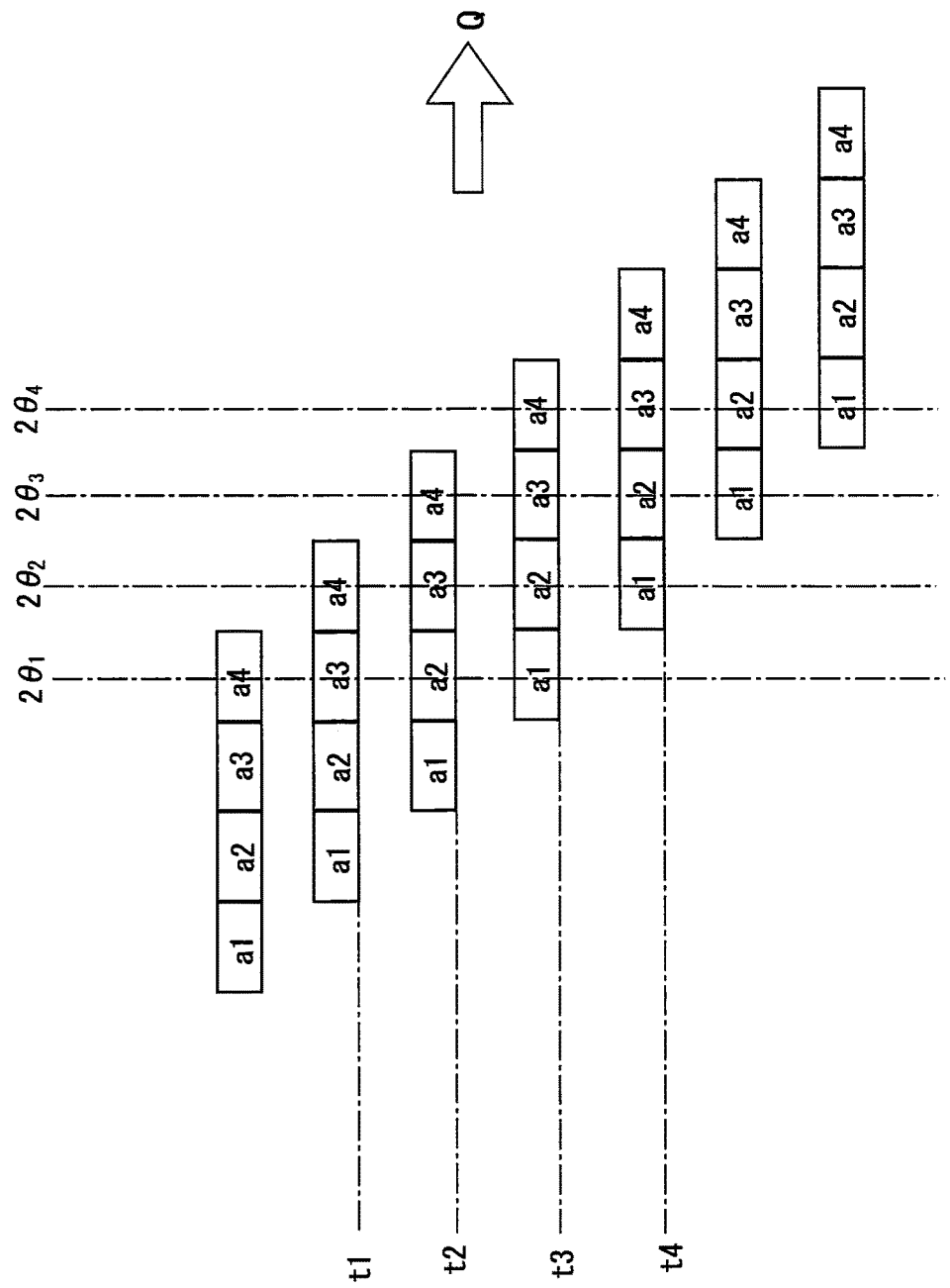
FIG. 26 is a diagram showing a TDI system.

In this TDI system, a plurality of detectors a1, a2, a3, a4 arranged side by side as shown in FIG. 26 are scanned in the arrangement direction (Q-direction in FIG. 26) to read out detection data from the respective detectors a1, a2, a3, a4, ..., aM at each of timings t1, t2, t3, t4, ..., tL, each timing corresponding to a time in which one detector is moved. The detection data of the respective detectors a1, a2, a3, a4, ..., aM are added with one another for each of scan angles $2\theta_1$, $2\theta_2$, $2\theta_3$, $2\theta_4$, ..., $2\theta N$, thereby acquiring the intensity of X-rays at each of the scan angles $2\theta_1$, $2\theta_2$, $2\theta_3$, $2\theta_4$, ..., $2\theta N$.

Specifically, a control signal is output from the goniometer controller 106 at every unit angle $\Delta\theta$ to rotate the respective rotation arms 32, 33 of the goniometer 30. At this time, a detection signal is read out from the one-dimensional X-ray detector by using, as a trigger, the control signal which is output from the goniometer controller 106 at every unit angle $\Delta\theta$. The detection signals from the one-dimensional X-ray detector are integrated while shifting the rotation angle $\theta$ of the respective rotation arms 32, 33 of the goniometer 30 at every constant time.

In the TDI system of this embodiment, the respective rotation arms 32 and 33 rotate while maintaining the relationship (rotation angles $\theta_X = \theta_D$) between the rotation arms 32 and 33. With this operation, reflected X-rays are detected while changing the incident angle $\theta$ ($=\theta_X$) of X-rays to the inspection target and also changing the detection angle position of the one-dimensional X-ray detector.

The acquisition of the X-ray detection data according to the TDI system may be performed by executing TDI-system software stored in the central processing unit 100. Furthermore, the acquisition of the X-ray detection data according to the TDI system can be also executed by hardware or a signal control circuit (firmware) incorporated in the one-dimensional X-ray detector.

When the divergence width of X-rays reflected from the inspection target is represented by $2\delta$, it is efficient that the scan range of TDI is limited as being equivalent to an angle divergence width $2\delta$. Here, M times of the pixel width of the one-dimensional X-ray detector corresponds to the detection range. At this time, when the execution range of the X-ray reflectivity measurement is set from 0 to $\theta_{max}$, the scan range $\theta_X$ of the goniometer ranges from $\theta-\delta$ to $\theta_{max}+\delta$. When the scan range of TDI is larger than $2\delta$, the scan range of the goniometer increases, and the through-put decreases.

Adoption of this TDI system not only promotes speedup of the measurement, but also enables detection of large detection intensities at respective scan angles.

Figure 27:
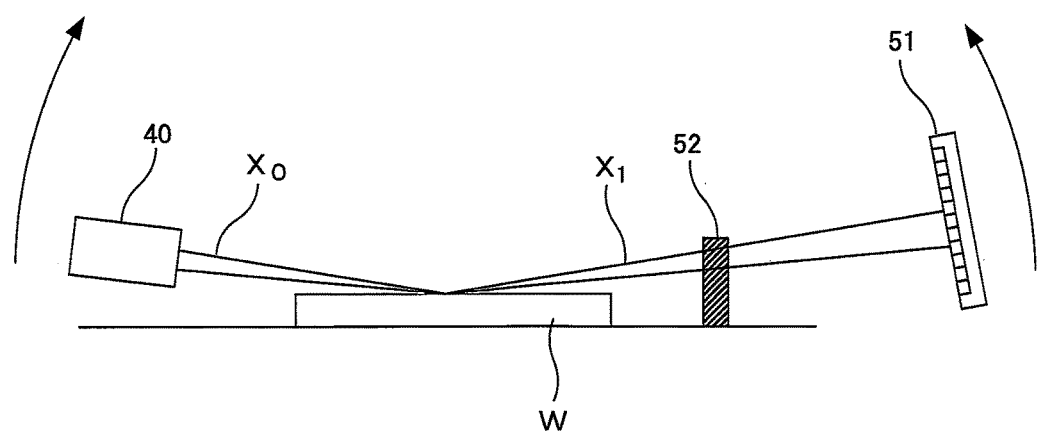
FIG. 27 is a diagram showing an embodiment associated with an improvement of the X-ray reflectivity measurement system.

FIG. 27 shows the outline of an X-ray reflectivity measurement system adopting the configurations described above.

As shown in FIG. 27, incident X-rays (focused X-rays) $X_0$ from the X-ray irradiation unit 40 is irradiated to the surface of a thin film sample W (for example, semiconductor wafer) so as to be incident very closely to the surface of the thin film sample W, and reflected X-rays $X_1$ reflected from the thin film sample W are detected by a one-dimensional X-ray detector 51. An X-ray irradiation unit having a confocal mirror as the X-ray optical element 43 as described above is adopted as the X-ray irradiation unit 40 (see FIGS. 6 to 15), for example. It is unnecessary to use the reflected X-rays $X_1$ while suppressing divergence of the reflected X-rays $X_1$ in the scan direction as shown in FIGS. 13 and 15, and conversely, reflected X-rays based on incident X-rays $X_0$ having a wide divergence angle can be simultaneously measured, thereby shortening the measurement time. The one-dimensional X-ray detector 51 is scanned according to the TDI system to acquire detection data of the X-rays.

As described above, when the scan range of TDI is narrowed to the angle divergence width $2\delta$ of reflected X-rays, it is unnecessary to provide a receiving slit (RS: Receiving Slit) for shielding scatter X-rays for the reflected X-rays $X_1$ reflected from the thin film sample W.

As described above, the X-ray reflectivity measurement based on the TDI system is performed without receiving slit by using the entire range of the reflected X-rays, so that the measurement speed can be remarkably increased.

On the other hand, when no receiving slit is provided, scattered X-rays from air or the surface of an inspection target, fluorescence X-rays occurring from the inspection target, etc. are incident to the one-dimensional X-ray detector, and increase background components (BG) other than reflected X-rays as a measurement target, so that the dynamic range of the one-dimensional X-ray detector 51 decreases.

Therefore, this embodiment adopts a configuration that an X-ray absorption member 52 is arranged as shown in FIG. 27 to attenuate the intensity of reflected X-rays $X_1$ reflected from the thin film sample W with the X-ray absorption member 52, and then the reflected X-rays $X_1$ are irradiated to the one-dimensional X-ray detector 51. The X-ray absorption member 52 is arranged so that reflected X-rays $X_1$ are irradiated to the one-dimensional X-ray detector 51 while attenuating the intensity X-rays $X_1$ which are at least totally reflected from the thin film sample. The X-ray absorption member 52 is preferably arranged so as to cover a range containing a total-reflection area Z shown in FIG. 25B and also extending to any scan angle $\theta d$ which does not reach a scan angle at which an oscillation pattern C important as measurement data appears. That is, in a scan angle range smaller than the scan angle $\theta d$, the X-rays $X_1$ having large intensities are reflected from the thin film sample W. The X-ray absorption member 52 is interposed on the optical path of the reflected X-rays $X_1$ having large intensities as described above to absorb a part of the reflected X-rays $X_1$ through the X-ray absorption member 52.

Figure 28A:
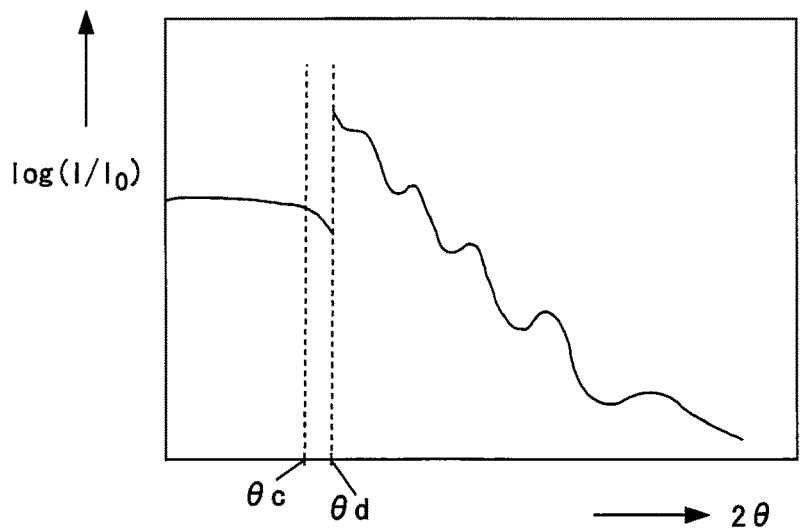
FIGS. 28A and 28B are diagrams showing an embodiment associated with the improvement of the X-ray reflectivity measurement system.
Figure 28B:
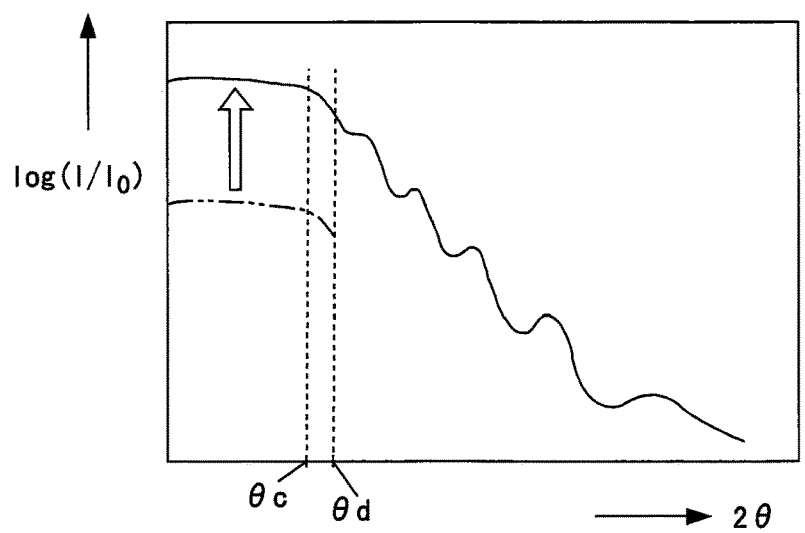

The intensities of the X-rays incident to the one-dimensional X-ray detector 51 decrease in the scan angle range through the X-ray absorption member 52 as shown in FIG. 28A. The X-ray detection data for this range are corrected by software to be raised by the intensity corresponding to the attenuation amount of the X-rays by the X-ray absorption member 52 as shown in FIG. 28B, thereby securing continuity with X-ray detection data in the scan angle range when the X-ray absorption member 52 is not interposed.

With the aforementioned configuration, the speedup of the X-ray reflectivity measurement based on the TDI system using the one-dimensional X-ray detector 51 can be accomplished.

Figure 29:
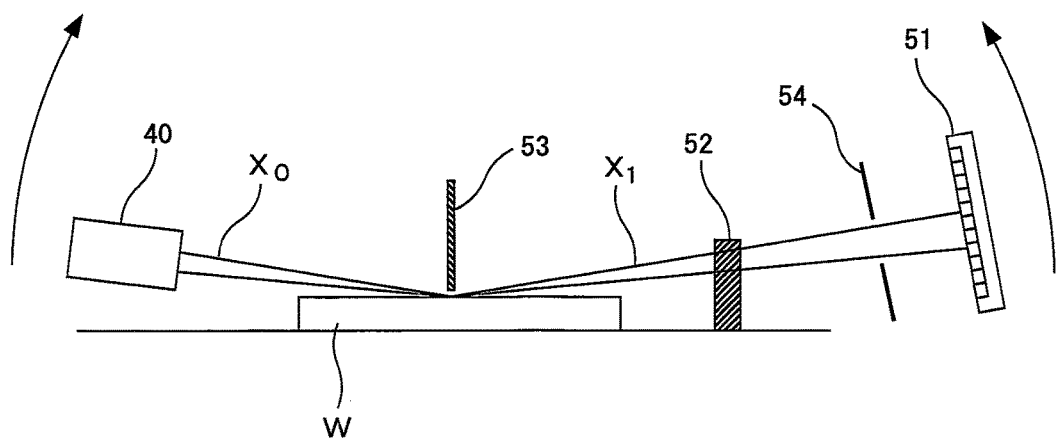
FIG. 29 is a schematic diagram showing an embodiment associated with a further improvement of the X-ray reflectivity measurement system shown in FIG. 27.

Furthermore, an X-ray shielding member 53 may be arranged to face the focusing position of the incident X-rays $X_0$ (or the emission position of the reflected X-rays $X_1$) on the surface of the thin film sample W as shown in FIG. 29. The X-ray shielding member 53 is formed of a material for preventing transmission of X-rays therethrough, configured in a wedge-like or plate-like shape and arranged to be perpendicular to the surface of the thin film sample W. A gap is formed between the surface of the thin film sample W and the X-ray shielding member 53, the gap being configured to be small to the extent that the incident X-rays $X_0$ incident to the thin film sample W (or the reflected X-rays $X_1$ from the thin film sample W) can barely pass through the gap.

By arranging the X-ray shielding member 53 as described above, scattered X-rays from air, ghost from a reflection mirror, etc. are shielded by the X-ray shielding member 53, and incidence of these X-rays other than the reflected X-rays to the one-dimensional X-ray detector 51 is suppressed, whereby the background (BG) components can be reduced.

With this configuration, the SN ratio can be enhanced mainly in a relatively large angle region where the intensity of reflected X-rays incident to the one-dimensional X-ray detector 51 is weakened, and thus the dynamic range of the X-ray reflectivity measurement can be enhanced.

In order to suppress the incidence of scattered X-rays from air or the surface of the thin film sample W, fluorescence X-rays occurring from the thin film sample W, etc. to the one-dimensional X-ray detector 51, a receiving slit 54 (SS: Scattering Slit) may be arranged in the optical path of the reflected X-rays $X_1$. In this case, only the receiving slit 54 may be arranged to form a gap through which the reflected X-rays $X_1$ can barely pass. However, when it is configured to dually shield scattered X-rays and fluorescence X-rays together with the X-ray shielding member 53 described above, incidence of the X-rays other than the reflected X-rays to the one-dimensional X-ray detector 51 can be further effectively suppressed, and the background (BG) components can be further reduced.

In the aforementioned embodiment, the X-ray reflectivity measurement is performed according to the TDI system using the one-dimensional X-ray detector. However, the X-ray reflectivity measurement may be performed according to the TDI system using a two-dimensional X-ray detector. This configuration is suitably applied to a case where two X-ray beams spreading in the width direction as shown in FIGS. 16 and 17 are used and a case where X-ray diffuse scattering is measured.

Furthermore, the X-ray absorption member 52 may be mounted on the receiving face of the one-dimensional X-ray detector or the two-dimensional X-ray detector. In this case, acquired X-ray detection data are corrected by software and integrated at every angle.

The invention claimed is:

1. An X-ray thin film inspection device comprising:
   a sample stage having an upper surface on which an inspection target is disposed;
   an image observing unit that is adapted to observe an image of the inspection target disposed on the upper surface of the sample stage;
   a positioning mechanism that is controlled based on an image observation result of the inspection target by the image observing unit to move the sample stage in two directions perpendicular to each other on a horizontal plane, the two directions being a height direction and an in-plane rotating direction;
   a goniometer having a first rotation member and a second rotation member that rotate along a virtual flat plane perpendicular to the upper surface of the sample stage;
   an X-ray irradiation unit installed on the first rotation member;
   an X-ray detector installed on the second rotation member; and
   a fluorescence X-ray detector that detects fluorescence X-rays generated from the inspection target upon irradiation of X-rays,
   wherein the X-ray irradiation unit comprises:
   an X-ray tube that radiates X-rays;
   an X-ray optical element comprising a confocal mirror that receives X-rays radiated from the X-ray tube, reflects a plurality of focused X-ray beams monochromatized at a specific wavelength, and focuses the plurality of focused X-ray beams to a preset focal point; and
   a slit mechanism that transmits therethrough an arbitrary number of focused X-ray beams out of the plurality of focused X-ray beams reflected from the X-ray optical element.

2. The X-ray thin film inspection device according to claim 1, wherein the X-ray irradiation unit has a configuration for adjusting rotation of the X-ray optical element around a center axis of the plurality of focused X-ray beams reflected from the X-ray optical element.

3. The X-ray thin film inspection device according to claim 2, wherein the slit mechanism is provided with two shielding plates formed of a material for shielding X-rays, and configured to pass the arbitrary number of focused X-ray beams through a gap formed between the shielding plates, and has a function of freely adjusting the extent of the gap.

4. The X-ray thin film inspection device according to claim 3, wherein the X-ray optical element is configured to reflect four rectangular focused X-ray beams at four corners of a virtual rectangle when viewed in optical path directions of X-rays reflected from the X-ray optical element.

5. The X-ray thin film inspection device according to claim 4, wherein with respect to two focused X-ray beams passing through the gap of the shielding plates out of the four focused X-ray beams reflected from the X-ray optical element, positional relationship of optical paths of the two focused X-ray beams is adjusted so as to make the two focused X-ray beams incident to an inspection target face of the inspection target so that a virtual plane containing the two focused X-ray beams is parallel to the inspection target face when viewed in the directions of the optical paths of the two focused X-ray beams.

6. The X-ray thin film inspection device according to claim 4, wherein the slit mechanism is configured to pass only one of the four focused X-ray beams reflected from the X-ray optical element through the gap of the shielding plates.

7. An X-ray thin film inspection device, comprising:
   a sample stage having an upper surface on which an inspection target is disposed;
   an image observing unit that is adapted to observe an image of the inspection target disposed on the upper surface of the sample stage;
   a positioning mechanism that is controlled based on an image observation result of the inspection target by the image observing unit to move the sample stage in two directions perpendicular to each other on a horizontal plane, the two directions being a height direction and an in-plane rotating direction;
   a goniometer having a first rotation member and a second rotation member that rotate along a virtual flat plane perpendicular to the upper surface of the sample stage;
   an X-ray irradiation unit installed on the first rotation member;
   an X-ray detector installed on the second rotation member; and
   a fluorescence X-ray detector that detects fluorescence X-rays generated from the inspection target upon irradiation of X-rays,
   wherein the X-ray irradiation unit comprises:
   an X-ray tube that radiates X-rays; and
   an X-ray optical element that is configured so that a double curved monochromator crystal plate comprising a semiconductor single crystal plate with a reflection surface having a high-order curved surface of a tertiary or higher order curved surface is fixed to a support block, makes X-rays radiated from the X-ray tube incident to the reflection surface and reflects focused X-rays monochromatized at a specific wavelength.

8. The X-ray thin film inspection device according to claim 7, wherein the X-ray optical element is configured to be curved in a length direction thereof for setting of an X-ray acceptance angle, and also curved in a width direction perpendicular to the length direction for setting of the X-ray acceptance angle.

9. An X-ray thin film inspection device, comprising:
a sample stage having an upper surface on which an inspection target is disposed;
an image observing unit that is adapted to observe an image of the inspection target disposed on the upper surface of the sample stage;
a positioning mechanism that is controlled based on an image observation result of the inspection target by the image observing unit to move the sample stage in two directions perpendicular to each other on a horizontal plane, the two directions being a height direction and an in-plane rotating direction;
a goniometer having a first rotation member and a second rotation member that rotate along a virtual flat plane perpendicular to the upper surface of the sample stage;
a plurality of X-ray irradiation units installed on the first rotation member;
an X-ray detector installed on the second rotation member; and
a fluorescence X-ray detector that detects fluorescence X-rays generated from the inspection target upon irradiation of X-rays,
wherein the X-ray irradiation units comprise a first X-ray irradiation unit and a second X-ray irradiation unit,
wherein the first X-ray irradiation unit comprises:
a first X-ray tube that radiates X-rays;
a first X-ray optical element comprising a confocal mirror that receives X-rays radiated from the X-ray tube, reflects a plurality of focused X-ray beams monochromatized at a specific wavelength, and focuses the plurality of focused X-ray beams to a preset focal point; and
a slit mechanism that transmits therethrough an arbitrary number of focused X-ray beams out of the plurality of focused X-ray beams reflected from the X-ray optical element,
wherein the second X-ray irradiation unit comprises:
a second X-ray tube that radiates X-rays; and
a second X-ray optical element that is configured so that a double curved monochromator crystal plate comprising a semiconductor single crystal plate with a reflection surface having a high-order curved surface of a tertiary or higher order curved surface is fixed to a support block, makes X-rays radiated from the X-ray tube incident to the reflection surface and reflects focused X-rays monochromatized at the specific wavelength, and wherein the X-ray irradiation units are installed on the first rotation member to be arranged in juxtaposition with each other in a rotation direction.

10. The X-ray thin film inspection device according to claim 6, wherein a one-dimensional X-ray detector is installed on the second rotation member, and an X-ray reflectivity measurement is performed by acquiring detection data of X-rays according to a TDI system.

11. The X-ray thin film inspection device according to claim 10, wherein the whole range of X-rays reflected from a thin film sample as the inspection target is received by the one-dimensional X-ray detector without receiving slit.

12. The X-ray thin film inspection device according to claim 11, wherein reflected X-rays that are at least totally reflected from the thin film sample is received by the one-dimensional X-ray detector while the intensity thereof is attenuated by an X-ray absorption member.

13. The X-ray thin film inspection device according to claim 12, wherein an X-ray shielding member is arranged at a position opposite to a focusing position of incident X-rays to the surface of the thin film sample or an emission position of reflected X-rays so as to form a gap through which incident X-rays incident to the thin film sample or reflected X-rays from the thin film sample can pass.

14. The X-ray thin film inspection device according to claim 12, wherein a receiving slit is arranged in an optical path of reflected X-rays from the thin film sample so as to form a gap through which the reflected X-rays can pass.

15. The X-ray thin film inspection device according to claim 5, wherein a two-dimensional X-ray detector is installed on the second rotation member, and an X-ray reflectivity measurement is performed by acquiring detection data of X-rays according to a TDI system.

16. The X-ray thin film inspection device according to claim 15, wherein the whole range of X-rays reflected from a thin film sample as the inspection target is received by the two-dimensional X-ray detector without receiving slit.

17. The X-ray thin film inspection device according to claim 16, wherein reflected X-rays that are at least totally reflected from the thin film sample is received by the two-dimensional X-ray detector while the intensity thereof is attenuated by an X-ray absorption member.

18. The X-ray thin film inspection device according to claim 17, wherein an X-ray shielding member is arranged at a position opposite to a focusing position of incident X-rays to the surface of the thin film sample or an emission position of reflected X-rays so as to form a gap through which incident X-rays incident to the thin film sample or reflected X-rays from the thin film sample can pass.

19. The X-ray thin film inspection device according to claim 17, wherein a receiving slit is arranged in an optical path of reflected X-rays from the thin film sample so as to form a gap through which the reflected X-rays can pass.

* * * * *